US008992541B2

(12) United States Patent
Ferreyro et al.

(10) Patent No.: US 8,992,541 B2
(45) Date of Patent: Mar. 31, 2015

(54) HYDRAULIC DEVICE FOR THE INJECTION OF BONE CEMENT IN PERCUTANEOUS VERTEBROPLASTY

(71) Applicant: DePuy Synthes Products, LLC, Raynham, MA (US)

(72) Inventors: Roque Humberto Irigoyen Ferreyro, New Orleans, LA (US); Mario Marquez Miranda, Oaxaca (MX)

(73) Assignee: Depuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 14/091,638

(22) Filed: Nov. 27, 2013

(65) Prior Publication Data

US 2014/0088605 A1   Mar. 27, 2014

Related U.S. Application Data

(63) Continuation of application No. 10/549,409, filed as application No. PCT/MX03/00027 on Mar. 14, 2003, now abandoned.

(51) Int. Cl.
*A61B 17/58* (2006.01)
*A61B 17/60* (2006.01)
(Continued)

(52) U.S. Cl.
CPC ......... *A61B 17/8819* (2013.01); *A61B 17/8822* (2013.01); *A61B 17/00234* (2013.01); *A61F 2002/4635* (2013.01); *A61M 5/31511* (2013.01); *A61M 5/31586* (2013.01)
USPC ........................................................ 606/94

(58) Field of Classification Search
USPC .................................................... 606/92–94
See application file for complete search history.

(56) References Cited

U.S. PATENT DOCUMENTS 229,932 A    7/1880   Witsil
370,335 A    9/1887   Hunter
(Continued)

FOREIGN PATENT DOCUMENTS

| AU | 9865136 A | 9/1998 |
|----|-----------|--------|
| AU | 724544 B2 | 9/2000 |

(Continued)

OTHER PUBLICATIONS

Fessler, Richard D. et al., "Vertebroplasty," Neurosurgical Operative Atlas 9:233-240 (2000).

(Continued)

*Primary Examiner* — Sameh Boles
(74) *Attorney, Agent, or Firm* — Nutter McClennen & Fish LLP

(57) ABSTRACT

The present invention relates to the medical field, in particular relates to the practice of percutaneous vertebroplasty where a pair of syringes in the distal extreme of a lengthened hydraulic device, are united by a camera of intermediate connection of larger diameter (pressure exerting body) or modified inverted syringe tube with a bolster, a hydraulic connecting tube of flexible material that transmits the pressure of the smaller diameter manual or impulsion syringe in the proximal extreme of the device toward the intermediate cylindrical larger diameter camera (pressure exerting body), this camera is in an inverted position with regard to the first syringe (fluid control), this intermediate camera has a moving piston longitudinal to the axis of the cylinder that is controlled with the first syringe (manual) and in cooperation with the atmospheric pressure. The injecting syringe loaded with bone cement is coupled with the bolster of the body of pressure, and to the needle that drives the cement toward the interior of the bone. The intermediate camera (pressure exerting body) together with the hydraulic tube and the manual syringe form a hydraulic press system (F/A=f/a) that allows to increase in a potential way the pressure exerted in the first syringe and to make the injection of polymethylmethacrylate (PMMA) at an approximate distance of 1.0 m to 1.5 m.

16 Claims, 7 Drawing Sheets

(51) Int. Cl.
*A61F 2/00* (2006.01)
*A61B 17/88* (2006.01)
*A61B 17/00* (2006.01)
*A61F 2/46* (2006.01)
*A61M 5/315* (2006.01)

(56) References Cited

U.S. PATENT DOCUMENTS

| | | |
|---|---|---|
| 817,973 A | 4/1906 | Hausmann |
| 833,044 A | 10/1906 | Goodhugh |
| 843,587 A | 2/1907 | DePew |
| 1,175,530 A | 3/1916 | Kirchoff |
| 1,612,281 A | 12/1926 | Goetz |
| 1,612,996 A | 1/1927 | Waagbo |
| 1,733,516 A | 10/1929 | Jamison |
| 1,894,274 A | 1/1933 | Jacques |
| 1,929,247 A | 10/1933 | Hein |
| 2,067,458 A | 1/1937 | Nichols |
| 2,123,712 A | 7/1938 | Clark |
| 2,283,915 A | 5/1942 | Cole |
| 2,394,488 A | 2/1946 | Rotter et al. |
| 2,425,867 A | 8/1947 | Davis |
| 2,435,647 A | 2/1948 | Engseth |
| 2,497,762 A | 2/1950 | Davis |
| 2,521,569 A | 9/1950 | Davis |
| 2,567,960 A | 9/1951 | Meyers et al. |
| 2,745,575 A | 5/1956 | Spencer |
| 2,773,500 A | 12/1956 | Young |
| 2,808,239 A | 10/1957 | Alfred |
| 2,874,877 A | 2/1959 | Spencer |
| 2,918,841 A | 12/1959 | Poupitch |
| 2,928,574 A | 3/1960 | Wagner |
| 2,970,773 A | 2/1961 | Horace et al. |
| 3,058,413 A | 10/1962 | Cavalieri |
| 3,063,449 A | 11/1962 | Schultz |
| 3,075,746 A | 1/1963 | Yablonski et al. |
| 3,108,593 A | 10/1963 | Glassman |
| 3,151,847 A | 10/1964 | Broomall |
| 3,198,194 A | 8/1965 | Wilburn |
| 3,216,616 A | 11/1965 | Blankenship, Jr. |
| 3,224,744 A | 12/1965 | Broomall |
| 3,225,760 A | 12/1965 | Di Cosola |
| 3,254,494 A | 6/1966 | Chartouni |
| 3,362,793 A | 1/1968 | Massoubre |
| 3,381,566 A | 5/1968 | Passer |
| 3,426,364 A | 2/1969 | Lumb |
| 3,515,873 A | 6/1970 | Higgins |
| 3,568,885 A | 3/1971 | Spencer |
| 3,572,556 A | 3/1971 | Pogacar |
| 3,615,240 A | 10/1971 | Sanz |
| 3,674,011 A | 7/1972 | Michel et al. |
| 3,701,350 A | 10/1972 | Guenther |
| 3,750,667 A | 8/1973 | Pshenichny et al. |
| 3,789,727 A | 2/1974 | Moran |
| 3,796,303 A | 3/1974 | Allet-Coche |
| 3,798,982 A | 3/1974 | Lundquist |
| 3,846,846 A | 11/1974 | Fischer |
| 3,850,158 A | 11/1974 | Elias et al. |
| 3,867,728 A | 2/1975 | Stubstad et al. |
| 3,873,008 A | 3/1975 | Jahn |
| 3,875,595 A | 4/1975 | Froning |
| 3,896,504 A | 7/1975 | Fischer |
| 3,901,408 A | 8/1975 | Boden et al. |
| 3,921,858 A | 11/1975 | Bemm |
| 3,931,914 A | 1/1976 | Hosaka et al. |
| 3,942,407 A | 3/1976 | Mortensen |
| 3,976,060 A | 8/1976 | Hildebrandt et al. |
| 3,993,250 A | 11/1976 | Shure |
| 4,011,602 A | 3/1977 | Rybicki et al. |
| 4,062,274 A | 12/1977 | Knab |
| 4,077,494 A | 3/1978 | Spaude et al. |
| 4,079,917 A | 3/1978 | Popeil |
| 4,090,640 A | 5/1978 | Smith et al. |
| 4,093,576 A | 6/1978 | deWijn |
| 4,105,145 A | 8/1978 | Capra |
| 4,115,346 A | 9/1978 | Gross et al. |
| 4,146,334 A | 3/1979 | Farrell |
| 4,168,787 A | 9/1979 | Stamper |
| 4,170,990 A | 10/1979 | Baumgart et al. |
| 4,180,070 A | 12/1979 | Genese |
| 4,185,072 A | 1/1980 | Puderbaugh et al. |
| 4,189,065 A | 2/1980 | Herold |
| 4,198,975 A | 4/1980 | Haller |
| 4,204,531 A | 5/1980 | Aginsky |
| 4,239,113 A | 12/1980 | Gross et al. |
| 4,250,887 A * | 2/1981 | Dardik et al. ................. 600/432 |
| 4,257,540 A | 3/1981 | Wegmann et al. |
| 4,268,639 A | 5/1981 | Seidel et al. |
| 4,274,163 A | 6/1981 | Malcom et al. |
| 4,276,878 A | 7/1981 | Storz |
| 4,277,184 A | 7/1981 | Solomon |
| 4,298,144 A | 11/1981 | Pressl |
| 4,309,777 A | 1/1982 | Patil |
| 4,312,343 A | 1/1982 | LeVeen et al. |
| 4,313,434 A | 2/1982 | Segal |
| 4,326,567 A | 4/1982 | Mistarz |
| 4,338,925 A | 7/1982 | Miller |
| 4,341,691 A | 7/1982 | Anuta |
| 4,346,708 A | 8/1982 | LeVeen et al. |
| 4,349,921 A | 9/1982 | Kuntz |
| 4,359,049 A | 11/1982 | Redl et al. |
| 4,373,217 A | 2/1983 | Draenert |
| 4,380,398 A | 4/1983 | Burgess |
| 4,400,170 A | 8/1983 | McNaughton et al. |
| 4,403,989 A | 9/1983 | Christensen et al. |
| 4,404,327 A | 9/1983 | Crugnola et al. |
| 4,405,249 A | 9/1983 | Scales |
| 4,409,966 A | 10/1983 | Lambrecht et al. |
| 4,453,539 A | 6/1984 | Raftopoulos et al. |
| 4,474,572 A | 10/1984 | McNaughton et al. |
| 4,475,856 A | 10/1984 | Toomingas |
| 4,476,866 A | 10/1984 | Chin |
| 4,487,602 A | 12/1984 | Christensen et al. |
| 4,494,535 A | 1/1985 | Haig |
| 4,500,658 A | 2/1985 | Fox |
| 4,503,169 A | 3/1985 | Randklev |
| 4,522,200 A | 6/1985 | Stednitz |
| D279,499 S | 7/1985 | Case |
| 4,543,966 A | 10/1985 | Islam et al. |
| 4,546,767 A | 10/1985 | Smith |
| 4,554,914 A | 11/1985 | Kapp et al. |
| 4,558,693 A | 12/1985 | Lash et al. |
| 4,562,598 A | 1/1986 | Kranz |
| 4,576,152 A | 3/1986 | Muller et al. |
| 4,588,583 A | 5/1986 | Pietsch et al. |
| 4,593,685 A | 6/1986 | McKay et al. |
| 4,595,006 A | 6/1986 | Burke et al. |
| 4,600,118 A | 7/1986 | Martin |
| 4,605,011 A | 8/1986 | Naslund |
| 4,632,101 A | 12/1986 | Freedland |
| 4,636,217 A | 1/1987 | Ogilvie et al. |
| 4,642,099 A | 2/1987 | Phillips et al. |
| 4,650,469 A | 3/1987 | Berg et al. |
| 4,651,904 A | 3/1987 | Schuckmann |
| 4,653,487 A | 3/1987 | Maale |
| 4,653,489 A | 3/1987 | Tronzo |
| 4,664,298 A | 5/1987 | Shew |
| 4,664,655 A | 5/1987 | Orentreich et al. |
| 4,668,220 A | 5/1987 | Hawrylenko |
| 4,668,295 A | 5/1987 | Bajpai |
| 4,670,008 A | 6/1987 | Von Albertini |
| 4,671,263 A | 6/1987 | Draenert |
| 4,676,655 A | 6/1987 | Handler |
| 4,676,781 A | 6/1987 | Phillips et al. |
| 4,686,973 A | 8/1987 | Frisch |
| 4,697,584 A | 10/1987 | Haynes |
| 4,697,929 A | 10/1987 | Muller |
| 4,704,035 A | 11/1987 | Kowalczyk |
| 4,710,179 A | 12/1987 | Haber et al. |
| 4,714,721 A | 12/1987 | Franek et al. |
| 4,717,383 A | 1/1988 | Phillips et al. |
| 4,718,910 A | 1/1988 | Draenert |
| 4,722,948 A | 2/1988 | Sanderson |
| 4,735,616 A | 4/1988 | Eibl et al. |

(56) References Cited

U.S. PATENT DOCUMENTS

| | | |
|---|---|---|
| 4,737,151 A | 4/1988 | Clement et al. |
| 4,747,832 A | 5/1988 | Buffet |
| 4,758,096 A | 7/1988 | Gunnarsson |
| 4,758,234 A | 7/1988 | Orentreich et al. |
| 4,759,769 A | 7/1988 | Hedman et al. |
| 4,762,515 A | 8/1988 | Grimm |
| 4,767,033 A | 8/1988 | Gemperle |
| 4,772,287 A | 9/1988 | Ray et al. |
| 4,782,118 A | 11/1988 | Fontanille et al. |
| 4,786,184 A | 11/1988 | Berezkina et al. |
| 4,791,150 A | 12/1988 | Braden et al. |
| 4,792,577 A | 12/1988 | Chen et al. |
| 4,804,023 A | 2/1989 | Frearson |
| 4,813,870 A | 3/1989 | Pitzen et al. |
| 4,815,454 A | 3/1989 | Dozier, Jr. |
| 4,815,632 A | 3/1989 | Ball et al. |
| 4,826,053 A | 5/1989 | Keller |
| 4,830,227 A | 5/1989 | Ball et al. |
| 4,837,279 A | 6/1989 | Arroyo |
| 4,854,312 A | 8/1989 | Raftopoulos et al. |
| 4,854,482 A | 8/1989 | Bergner |
| 4,854,716 A | 8/1989 | Ziemann et al. |
| 4,863,072 A | 9/1989 | Perler |
| 4,869,906 A | 9/1989 | Dingeldein et al. |
| 4,872,936 A | 10/1989 | Engelbrecht |
| 4,892,231 A | 1/1990 | Ball |
| 4,892,550 A | 1/1990 | Huebsch |
| 4,902,649 A | 2/1990 | Kimura et al. |
| 4,904,260 A | 2/1990 | Ray et al. |
| 4,908,017 A | 3/1990 | Howson et al. |
| 4,910,259 A | 3/1990 | Kindt-Larsen et al. |
| 4,927,866 A | 5/1990 | Purrmann et al. |
| 4,932,969 A | 6/1990 | Frey et al. |
| 4,935,029 A | 6/1990 | Matsutani et al. |
| 4,944,065 A | 7/1990 | Svanberg et al. |
| 4,944,726 A | 7/1990 | Hilal et al. |
| 4,946,077 A | 8/1990 | Olsen |
| 4,946,285 A | 8/1990 | Vennemeyer |
| 4,946,901 A | 8/1990 | Lechner et al. |
| 4,961,647 A | 10/1990 | Coutts et al. |
| 4,966,601 A | 10/1990 | Draenert |
| 4,968,303 A | 11/1990 | Clarke et al. |
| 4,969,888 A | 11/1990 | Scholten et al. |
| 4,973,168 A | 11/1990 | Chan |
| 4,973,301 A | 11/1990 | Nissenkorn |
| 4,973,334 A | 11/1990 | Ziemann |
| 4,978,336 A | 12/1990 | Capozzi et al. |
| 4,983,164 A | 1/1991 | Hook et al. |
| 4,994,065 A | 2/1991 | Gibbs et al. |
| 4,995,868 A | 2/1991 | Brazier |
| 5,004,501 A | 4/1991 | Faccioli et al. |
| 5,006,112 A | 4/1991 | Metzner |
| 5,012,066 A | 4/1991 | Matsutani et al. |
| 5,015,233 A | 5/1991 | McGough et al. |
| 5,018,919 A | 5/1991 | Stephan |
| 5,022,563 A | 6/1991 | Marchitto et al. |
| 5,024,232 A | 6/1991 | Smid et al. |
| 5,028,141 A | 7/1991 | Stiegelmann |
| 5,037,473 A | 8/1991 | Antonucci et al. |
| 5,049,157 A | 9/1991 | Mittelmeier et al. |
| 5,051,482 A | 9/1991 | Tepic |
| 5,059,193 A | 10/1991 | Kuslich |
| 5,059,199 A | 10/1991 | Okada et al. |
| 5,061,128 A | 10/1991 | Jahr et al. |
| 5,071,040 A | 12/1991 | Laptewicz, Jr. |
| 5,074,871 A | 12/1991 | Groshong |
| 5,078,919 A | 1/1992 | Ashley et al. |
| 5,092,888 A | 3/1992 | Iwamoto et al. |
| 5,102,413 A | 4/1992 | Poddar |
| 5,108,403 A | 4/1992 | Stern |
| 5,108,404 A | 4/1992 | Scholten et al. |
| 5,112,333 A | 5/1992 | Fixel |
| 5,114,240 A | 5/1992 | Kindt-Larsen et al. |
| 5,116,335 A | 5/1992 | Hannon et al. |
| 5,122,400 A | 6/1992 | Stewart |
| 5,123,926 A | 6/1992 | Pisharodi |
| 5,125,971 A | 6/1992 | Nonami et al. |
| 5,131,382 A | 7/1992 | Meyer |
| 5,141,496 A | 8/1992 | Dalto et al. |
| 5,145,250 A | 9/1992 | Planck et al. |
| 5,147,903 A | 9/1992 | Podszun et al. |
| 5,171,248 A | 12/1992 | Ellis |
| 5,171,278 A | 12/1992 | Pisharodi |
| 5,181,918 A | 1/1993 | Brandhorst et al. |
| 5,188,259 A | 2/1993 | Petit |
| 5,190,191 A | 3/1993 | Reyman |
| 5,192,327 A | 3/1993 | Brantigan |
| 5,193,907 A | 3/1993 | Faccioli et al. |
| 5,209,753 A | 5/1993 | Biedermann et al. |
| 5,217,147 A | 6/1993 | Kaufman |
| 5,219,897 A | 6/1993 | Murray |
| 5,236,445 A | 8/1993 | Hayhurst et al. |
| 5,242,983 A | 9/1993 | Kennedy et al. |
| 5,252,301 A | 10/1993 | Nilson et al. |
| 5,254,092 A | 10/1993 | Polyak |
| 5,258,420 A | 11/1993 | Posey-Dowty et al. |
| 5,264,215 A | 11/1993 | Nakabayashi et al. |
| 5,268,001 A | 12/1993 | Nicholson et al. |
| 5,269,762 A | 12/1993 | Armbruster et al. |
| 5,275,214 A | 1/1994 | Rehberger |
| 5,276,070 A | 1/1994 | Arroyo |
| 5,277,339 A | 1/1994 | Shew et al. |
| 5,279,555 A | 1/1994 | Lifshey |
| 5,290,260 A | 3/1994 | Stines |
| 5,295,980 A | 3/1994 | Ersek |
| 5,302,020 A | 4/1994 | Kruse |
| 5,303,718 A | 4/1994 | Krajicek |
| 5,304,147 A | 4/1994 | Johnson et al. |
| 5,318,532 A | 6/1994 | Frassica |
| 5,328,262 A | 7/1994 | Lidgren et al. |
| 5,328,362 A | 7/1994 | Watson et al. |
| 5,331,972 A | 7/1994 | Wadhwani et al. |
| 5,333,951 A | 8/1994 | Wakoh |
| 5,334,184 A | 8/1994 | Bimman |
| 5,334,626 A | 8/1994 | Lin |
| 5,336,699 A | 8/1994 | Cooke et al. |
| 5,336,700 A | 8/1994 | Murray |
| 5,344,232 A | 9/1994 | Nelson et al. |
| 5,348,391 A | 9/1994 | Murray |
| 5,348,548 A | 9/1994 | Meyer et al. |
| 5,350,372 A | 9/1994 | Ikeda et al. |
| 5,354,287 A | 10/1994 | Wacks |
| 5,356,382 A | 10/1994 | Picha et al. |
| 5,368,046 A | 11/1994 | Scarfone et al. |
| 5,368,386 A | 11/1994 | Murray |
| 5,370,221 A | 12/1994 | Magnusson et al. |
| 5,372,583 A | 12/1994 | Roberts et al. |
| 5,374,427 A | 12/1994 | Stille et al. |
| 5,376,123 A | 12/1994 | Klaue et al. |
| 5,380,772 A | 1/1995 | Hasegawa et al. |
| 5,385,081 A | 1/1995 | Sneddon |
| 5,385,566 A | 1/1995 | Ullmark |
| 5,387,191 A | 2/1995 | Hemstreet et al. |
| 5,390,683 A | 2/1995 | Pisharodi |
| 5,395,167 A | 3/1995 | Murray |
| 5,395,326 A | 3/1995 | Haber et al. |
| 5,398,483 A | 3/1995 | Smith et al. |
| 5,401,806 A | 3/1995 | Braden et al. |
| 5,411,180 A | 5/1995 | Dumelle |
| 5,415,474 A | 5/1995 | Nelson et al. |
| 5,423,850 A | 6/1995 | Berger |
| 5,431,654 A | 7/1995 | Nic |
| 5,435,645 A | 7/1995 | Faccioli et al. |
| 5,443,182 A | 8/1995 | Tanaka et al. |
| 5,445,639 A | 8/1995 | Kuslich et al. |
| 5,450,924 A | 9/1995 | Tseng |
| 5,454,365 A | 10/1995 | Bonutti |
| 5,456,267 A | 10/1995 | Stark |
| 5,468,245 A | 11/1995 | Vargas, III |
| 5,480,400 A | 1/1996 | Berger |
| 5,480,403 A | 1/1996 | Lee et al. |
| 5,482,187 A | 1/1996 | Poulsen et al. |
| 5,492,247 A | 2/1996 | Shu et al. |
| 5,494,349 A | 2/1996 | Seddon |

(56) References Cited

U.S. PATENT DOCUMENTS

| | | |
|---|---|---|
| 5,501,374 A | 3/1996 | Laufer et al. |
| 5,501,520 A | 3/1996 | Lidgren et al. |
| 5,501,695 A | 3/1996 | Anspach, Jr. et al. |
| 5,512,610 A | 4/1996 | Lin |
| 5,514,135 A | 5/1996 | Earle |
| 5,514,137 A | 5/1996 | Coutts |
| 5,518,498 A | 5/1996 | Lindenberg et al. |
| 5,520,690 A | 5/1996 | Errico et al. |
| 5,522,816 A | 6/1996 | Dinello et al. |
| 5,522,899 A | 6/1996 | Michelson |
| 5,526,853 A | 6/1996 | McPhee et al. |
| 5,531,519 A | 7/1996 | Earle |
| 5,534,028 A | 7/1996 | Bao et al. |
| 5,536,262 A | 7/1996 | Velasquez |
| 5,545,460 A | 8/1996 | Tanaka et al. |
| 5,548,001 A | 8/1996 | Podszun et al. |
| 5,549,380 A | 8/1996 | Lidgren et al. |
| 5,549,381 A | 8/1996 | Hays et al. |
| 5,549,679 A | 8/1996 | Kuslich |
| 5,551,778 A | 9/1996 | Hauke et al. |
| 5,554,101 A | 9/1996 | Matula et al. |
| 5,556,201 A | 9/1996 | Veltrop et al. |
| 5,558,136 A | 9/1996 | Orrico |
| 5,558,639 A | 9/1996 | Gangemi et al. |
| 5,571,189 A | 11/1996 | Kuslich |
| 5,573,265 A | 11/1996 | Pradel et al. |
| 5,578,035 A | 11/1996 | Lin |
| 5,586,821 A | 12/1996 | Bonitati et al. |
| 5,588,745 A | 12/1996 | Tanaka et al. |
| 5,591,197 A | 1/1997 | Orth et al. |
| 5,601,557 A | 2/1997 | Hayhurst |
| 5,603,701 A | 2/1997 | Fischer |
| 5,609,637 A | 3/1997 | Biedermann et al. |
| 5,624,184 A | 4/1997 | Chan |
| 5,630,806 A | 5/1997 | Inagaki et al. |
| 5,634,880 A | 6/1997 | Feldman et al. |
| 5,637,097 A | 6/1997 | Yoon |
| 5,638,997 A | 6/1997 | Hawkins et al. |
| 5,641,010 A | 6/1997 | Maier |
| 5,645,598 A | 7/1997 | Brosnahan, III |
| 5,647,856 A | 7/1997 | Eykmann et al. |
| 5,653,686 A | 8/1997 | Coulter et al. |
| 5,658,310 A | 8/1997 | Berger |
| 5,660,186 A | 8/1997 | Bachir |
| 5,665,067 A | 9/1997 | Linder et al. |
| 5,681,317 A | 10/1997 | Caldarise |
| 5,683,451 A | 11/1997 | Lenker et al. |
| 5,685,826 A | 11/1997 | Bonutti |
| 5,690,606 A | 11/1997 | Slotman |
| 5,693,100 A | 12/1997 | Pisharodi |
| 5,697,977 A | 12/1997 | Pisharodi |
| 5,698,611 A | 12/1997 | Okada et al. |
| 5,702,448 A | 12/1997 | Buechel et al. |
| 5,704,895 A | 1/1998 | Scott et al. |
| 5,707,390 A | 1/1998 | Bonutti |
| 5,718,707 A | 2/1998 | Mikhail |
| 5,720,753 A | 2/1998 | Sander et al. |
| 5,725,341 A | 3/1998 | Hofmeister |
| 5,725,529 A | 3/1998 | Nicholson et al. |
| 5,747,553 A | 5/1998 | Guzauskas |
| 5,752,935 A | 5/1998 | Robinson et al. |
| 5,752,969 A | 5/1998 | Cunci et al. |
| 5,752,974 A | 5/1998 | Rhee et al. |
| 5,755,732 A | 5/1998 | Green et al. |
| 5,759,186 A | 6/1998 | Bachmann et al. |
| 5,763,092 A | 6/1998 | Lee et al. |
| 5,779,356 A | 7/1998 | Chan |
| 5,782,713 A | 7/1998 | Yang |
| 5,782,747 A | 7/1998 | Zimmon |
| 5,782,830 A | 7/1998 | Farris |
| 5,782,838 A | 7/1998 | Beyar et al. |
| 5,785,647 A | 7/1998 | Tompkins et al. |
| 5,792,044 A | 8/1998 | Foley et al. |
| 5,795,922 A | 8/1998 | Demian et al. |
| 5,797,678 A | 8/1998 | Murray |
| 5,800,169 A | 9/1998 | Muhlbauer |
| 5,800,409 A | 9/1998 | Bruce |
| 5,800,549 A | 9/1998 | Bao et al. |
| 5,800,550 A | 9/1998 | Sertich |
| 5,820,321 A | 10/1998 | Gruber |
| 5,824,087 A | 10/1998 | Aspden et al. |
| 5,826,713 A | 10/1998 | Sunago et al. |
| 5,826,753 A | 10/1998 | Fehlig et al. |
| 5,827,289 A | 10/1998 | Reiley et al. |
| 5,829,875 A | 11/1998 | Hagel et al. |
| 5,830,194 A | 11/1998 | Anwar et al. |
| 5,836,306 A | 11/1998 | Duane et al. |
| 5,839,621 A | 11/1998 | Tada |
| 5,842,785 A | 12/1998 | Brown et al. |
| 5,865,802 A | 2/1999 | Yoon et al. |
| 5,876,116 A | 3/1999 | Barker et al. |
| 5,876,457 A | 3/1999 | Picha et al. |
| 5,882,340 A | 3/1999 | Yoon |
| 5,884,818 A | 3/1999 | Campbell |
| 5,893,488 A | 4/1999 | Hoag et al. |
| 5,893,850 A | 4/1999 | Cachia |
| 5,902,839 A | 5/1999 | Lautenschlager et al. |
| 5,911,721 A | 6/1999 | Nicholson et al. |
| 5,918,702 A | 7/1999 | Cheng et al. |
| 5,918,770 A | 7/1999 | Camm et al. |
| 5,925,051 A | 7/1999 | Mikhail |
| 5,928,239 A | 7/1999 | Mirza |
| 5,931,347 A | 8/1999 | Haubrich |
| 5,941,851 A | 8/1999 | Coffey et al. |
| 5,954,671 A | 9/1999 | O'Neill |
| 5,954,728 A | 9/1999 | Heller et al. |
| 5,961,211 A | 10/1999 | Barker et al. |
| 5,968,008 A | 10/1999 | Grams |
| 5,968,044 A | 10/1999 | Nicholson et al. |
| 5,968,999 A | 10/1999 | Ramp et al. |
| 5,972,015 A | 10/1999 | Scribner et al. |
| 5,980,527 A | 11/1999 | Cohen et al. |
| 5,993,535 A | 11/1999 | Sawamura et al. |
| 5,997,544 A | 12/1999 | Nies et al. |
| 6,004,325 A | 12/1999 | Vargas, III |
| 6,007,496 A | 12/1999 | Brannon |
| 6,017,349 A | 1/2000 | Heller et al. |
| 6,019,765 A | 2/2000 | Thornhill et al. |
| 6,019,776 A | 2/2000 | Preissman et al. |
| 6,019,789 A | 2/2000 | Dinh et al. |
| 6,020,396 A | 2/2000 | Jacobs |
| 6,033,105 A | 3/2000 | Barker et al. |
| 6,033,411 A | 3/2000 | Preissman |
| 6,039,761 A | 3/2000 | Li et al. |
| 6,040,408 A | 3/2000 | Koole |
| 6,041,977 A | 3/2000 | Lisi |
| 6,042,262 A | 3/2000 | Hajianpour |
| 6,045,555 A | 4/2000 | Smith et al. |
| 6,048,346 A | 4/2000 | Reiley et al. |
| 6,049,026 A | 4/2000 | Muschler |
| 6,075,067 A | 6/2000 | Lidgren |
| 6,080,579 A | 6/2000 | Hanley, Jr. et al. |
| 6,080,801 A | 6/2000 | Draenert et al. |
| 6,080,811 A | 6/2000 | Schehlmann et al. |
| 6,083,229 A | 7/2000 | Constantz et al. |
| 6,086,594 A | 7/2000 | Brown |
| 6,103,779 A | 8/2000 | Guzauskas |
| 6,116,773 A | 9/2000 | Murray |
| 6,120,174 A | 9/2000 | Hoag et al. |
| 6,124,373 A | 9/2000 | Peter et al. |
| 6,126,689 A | 10/2000 | Brett |
| 6,127,597 A | 10/2000 | Beyar et al. |
| 6,129,763 A | 10/2000 | Chauvin et al. |
| 6,132,396 A | 10/2000 | Antanavich et al. |
| 6,136,038 A | 10/2000 | Raab |
| 6,139,509 A | 10/2000 | Yuan et al. |
| 6,142,998 A | 11/2000 | Smith et al. |
| 6,146,401 A | 11/2000 | Yoon et al. |
| 6,149,651 A | 11/2000 | Drewry et al. |
| 6,149,655 A | 11/2000 | Constantz et al. |
| 6,149,664 A | 11/2000 | Kurz |
| 6,160,033 A | 12/2000 | Nies |
| 6,161,955 A | 12/2000 | Rademaker |
| 6,168,597 B1 | 1/2001 | Biedermann et al. |

(56) References Cited

U.S. PATENT DOCUMENTS

| | | |
|---|---|---|
| 6,174,935 B1 | 1/2001 | Matsunae et al. |
| 6,176,607 B1 | 1/2001 | Hajianpour |
| 6,183,441 B1 | 2/2001 | Kriesel et al. |
| 6,183,516 B1 | 2/2001 | Burkinshaw et al. |
| 6,187,015 B1 | 2/2001 | Brenneman |
| 6,190,381 B1 | 2/2001 | Olsen et al. |
| 6,210,031 B1 | 4/2001 | Murray |
| 6,214,012 B1 | 4/2001 | Karpman et al. |
| 6,214,016 B1 | 4/2001 | Williams et al. |
| 6,214,037 B1 | 4/2001 | Mitchell et al. |
| 6,217,566 B1 | 4/2001 | Ju et al. |
| 6,217,581 B1 | 4/2001 | Tolson |
| 6,217,608 B1 | 4/2001 | Penn et al. |
| 6,221,029 B1 | 4/2001 | Mathis et al. |
| 6,224,604 B1 | 5/2001 | Suddaby |
| 6,228,049 B1 | 5/2001 | Schroeder et al. |
| 6,228,068 B1 | 5/2001 | Yoon |
| 6,228,082 B1 | 5/2001 | Baker et al. |
| 6,231,615 B1 | 5/2001 | Preissman |
| 6,235,043 B1 | 5/2001 | Reiley et al. |
| 6,238,399 B1 | 5/2001 | Heller et al. |
| 6,241,734 B1 | 6/2001 | Scribner et al. |
| 6,245,101 B1 | 6/2001 | Drasler et al. |
| 6,248,110 B1 | 6/2001 | Reiley et al. |
| 6,254,268 B1 | 7/2001 | Long |
| 6,261,289 B1 | 7/2001 | Levy |
| 6,264,618 B1 | 7/2001 | Landi et al. |
| 6,264,659 B1 | 7/2001 | Ross et al. |
| 6,264,660 B1 | 7/2001 | Schmidt et al. |
| 6,273,916 B1 | 8/2001 | Murphy |
| 6,281,271 B1 | 8/2001 | Rumphorst et al. |
| 6,309,395 B1 | 10/2001 | Smith et al. |
| 6,309,420 B1 | 10/2001 | Preissman |
| 6,312,149 B1 | 11/2001 | Sjovall et al. |
| 6,325,812 B1 | 12/2001 | Dubrul et al. |
| 6,348,055 B1 | 2/2002 | Preissman |
| 6,348,518 B1 | 2/2002 | Montgomery |
| 6,350,271 B1 | 2/2002 | Kurz et al. |
| 6,361,539 B1 | 3/2002 | Heller et al. |
| 6,364,865 B1 | 4/2002 | Lavi et al. |
| 6,367,962 B1 | 4/2002 | Mizutani et al. |
| 6,375,659 B1 | 4/2002 | Erbe et al. |
| 6,375,682 B1 | 4/2002 | Fleischmann et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,402,701 B1 | 6/2002 | Kaplan et al. |
| 6,402,758 B1 | 6/2002 | Tolson |
| 6,406,175 B1 | 6/2002 | Marino |
| 6,409,972 B1 | 6/2002 | Chan |
| 6,410,612 B1 | 6/2002 | Hatanaka |
| 6,425,887 B1 | 7/2002 | McGuckin et al. |
| 6,431,743 B1 | 8/2002 | Mizutani et al. |
| 6,433,037 B1 | 8/2002 | Guzauskas |
| 6,436,143 B1 | 8/2002 | Ross et al. |
| 6,439,439 B1 | 8/2002 | Rickard et al. |
| 6,443,334 B1 | 9/2002 | John et al. |
| 6,447,478 B1 | 9/2002 | Maynard |
| 6,450,973 B1 | 9/2002 | Murphy |
| 6,458,117 B1 | 10/2002 | Pollins, Sr. |
| 6,479,565 B1 | 11/2002 | Stanley |
| 6,488,667 B1 | 12/2002 | Murphy |
| 6,494,868 B2 | 12/2002 | Amar |
| 6,500,182 B2 | 12/2002 | Foster |
| 6,502,608 B1 | 1/2003 | Burchett et al. |
| 6,527,144 B2 | 3/2003 | Ritsche et al. |
| 6,550,957 B2 | 4/2003 | Mizutani et al. |
| 6,554,833 B2 | 4/2003 | Levy et al. |
| 6,572,256 B2 | 6/2003 | Seaton et al. |
| 6,575,331 B1 | 6/2003 | Peeler et al. |
| 6,575,919 B1 | 6/2003 | Reiley et al. |
| 6,582,439 B1 | 6/2003 | Sproul |
| 6,592,559 B1 | 7/2003 | Pakter et al. |
| 6,595,967 B2 | 7/2003 | Kramer |
| 6,599,293 B2 | 7/2003 | Tague et al. |
| 6,599,520 B2 | 7/2003 | Scarborough et al. |
| 6,613,018 B2 | 9/2003 | Bagga et al. |
| 6,613,054 B2 | 9/2003 | Scribner et al. |
| 6,626,912 B2 | 9/2003 | Speitling |
| 6,641,587 B2 | 11/2003 | Scribner et al. |
| 6,645,213 B2 | 11/2003 | Sand et al. |
| 6,662,969 B2 | 12/2003 | Peeler et al. |
| 6,676,664 B1 | 1/2004 | Al-Assir |
| 6,689,823 B1 | 2/2004 | Bellare et al. |
| 6,702,455 B2 | 3/2004 | Vendrely et al. |
| 6,712,853 B2 | 3/2004 | Kuslich |
| 6,716,216 B1 | 4/2004 | Boucher et al. |
| 6,719,761 B1 | 4/2004 | Reiley et al. |
| 6,720,417 B1 | 4/2004 | Walter |
| 6,730,095 B2 | 5/2004 | Olson, Jr. et al. |
| 6,752,180 B2 | 6/2004 | Delay |
| 6,758,837 B2 | 7/2004 | Peclat et al. |
| 6,759,449 B2 | 7/2004 | Kimura et al. |
| 6,767,973 B2 | 7/2004 | Suau et al. |
| 6,770,079 B2 | 8/2004 | Bhatnagar et al. |
| 6,779,566 B2 | 8/2004 | Engel |
| 6,780,175 B1 | 8/2004 | Sachdeva et al. |
| 6,783,515 B1 | 8/2004 | Miller et al. |
| 6,787,584 B2 | 9/2004 | Jia et al. |
| 6,796,987 B2 | 9/2004 | Tague et al. |
| 6,852,439 B2 | 2/2005 | Frank et al. |
| 6,874,927 B2 | 4/2005 | Foster |
| 6,875,219 B2 | 4/2005 | Arramon et al. |
| 6,887,246 B2 | 5/2005 | Bhatnagar et al. |
| 6,916,308 B2 | 7/2005 | Dixon et al. |
| 6,957,747 B2 | 10/2005 | Peeler et al. |
| 6,974,247 B2 | 12/2005 | Frei et al. |
| 6,974,416 B2 | 12/2005 | Booker et al. |
| 6,979,341 B2 | 12/2005 | Scribner et al. |
| 6,979,352 B2 | 12/2005 | Reynolds |
| 6,994,465 B2 | 2/2006 | Tague et al. |
| 6,997,930 B1 | 2/2006 | Jaggi et al. |
| 7,008,433 B2 | 3/2006 | Voellmicke et al. |
| 7,025,771 B2 | 4/2006 | Kuslich et al. |
| 7,029,163 B2 | 4/2006 | Barker et al. |
| 7,044,954 B2 | 5/2006 | Reiley et al. |
| 7,048,743 B2 | 5/2006 | Miller et al. |
| 7,066,942 B2 | 6/2006 | Treace |
| 7,087,040 B2 | 8/2006 | McGuckin, Jr. et al. |
| 7,091,258 B2 | 8/2006 | Neubert et al. |
| 7,097,648 B1 | 8/2006 | Globerman et al. |
| 7,112,205 B2 | 9/2006 | Carrison |
| 7,116,121 B1 | 10/2006 | Holcombe et al. |
| 7,252,671 B2 | 8/2007 | Scribner et al. |
| 7,264,622 B2 | 9/2007 | Michelson |
| 7,270,667 B2 | 9/2007 | Faccioli et al. |
| 7,278,778 B2 | 10/2007 | Sand |
| 7,326,203 B2 | 2/2008 | Papineau et al. |
| 7,456,024 B2 | 11/2008 | Dahm et al. |
| 7,559,932 B2 | 7/2009 | Truckai et al. |
| 7,572,263 B2 | 8/2009 | Preissman |
| 7,575,577 B2 | 8/2009 | Boyd et al. |
| 7,604,618 B2 | 10/2009 | Dixon et al. |
| 7,666,205 B2 | 2/2010 | Weikel et al. |
| 7,678,116 B2 | 3/2010 | Truckai et al. |
| 7,717,918 B2 | 5/2010 | Truckai et al. |
| 7,722,620 B2 | 5/2010 | Truckai et al. |
| 8,066,713 B2 | 11/2011 | DiMauro et al. |
| 8,070,753 B2 | 12/2011 | Truckai et al. |
| 8,333,773 B2 | 12/2012 | DiMauro et al. |
| 8,360,629 B2 | 1/2013 | Globerman et al. |
| 8,361,078 B2 | 1/2013 | Beyar et al. |
| 8,415,407 B2 | 4/2013 | Beyar et al. |
| 8,540,722 B2 | 9/2013 | Beyar et al. |
| 2001/0012968 A1 | 8/2001 | Preissman |
| 2001/0034527 A1 | 10/2001 | Scribner et al. |
| 2002/0008122 A1 | 1/2002 | Ritsche et al. |
| 2002/0010471 A1 | 1/2002 | Wironen et al. |
| 2002/0010472 A1 | 1/2002 | Kuslich et al. |
| 2002/0013553 A1 | 1/2002 | Pajunk et al. |
| 2002/0049448 A1 | 4/2002 | Sand et al. |
| 2002/0049449 A1 | 4/2002 | Bhatnagar et al. |
| 2002/0058947 A1 | 5/2002 | Hochschuler et al. |
| 2002/0067658 A1 | 6/2002 | Vendrely et al. |

(56) References Cited

U.S. PATENT DOCUMENTS

| | | |
|---|---|---|
| 2002/0068939 A1 | 6/2002 | Levy et al. |
| 2002/0068974 A1 | 6/2002 | Kuslich et al. |
| 2002/0068975 A1 | 6/2002 | Teitelbaum et al. |
| 2002/0072768 A1 | 6/2002 | Ginn |
| 2002/0099384 A1 | 7/2002 | Scribner et al. |
| 2002/0099385 A1 | 7/2002 | Ralph et al. |
| 2002/0118595 A1 | 8/2002 | Miller et al. |
| 2002/0156483 A1 | 10/2002 | Voellmicke et al. |
| 2002/0161373 A1 | 10/2002 | Osorio et al. |
| 2002/0177866 A1 | 11/2002 | Weikel et al. |
| 2002/0188300 A1 | 12/2002 | Arramon et al. |
| 2002/0191487 A1 | 12/2002 | Sand |
| 2003/0009177 A1 | 1/2003 | Middleman et al. |
| 2003/0018339 A1 | 1/2003 | Higueras et al. |
| 2003/0031698 A1 | 2/2003 | Roeder et al. |
| 2003/0032929 A1 | 2/2003 | McGuckin |
| 2003/0036763 A1 | 2/2003 | Bhatnagar et al. |
| 2003/0040718 A1 | 2/2003 | Kust et al. |
| 2003/0050644 A1 | 3/2003 | Boucher et al. |
| 2003/0050702 A1 | 3/2003 | Berger |
| 2003/0078589 A1 | 4/2003 | Preissman |
| 2003/0109883 A1 | 6/2003 | Matsuzaki et al. |
| 2003/0109884 A1 | 6/2003 | Tague et al. |
| 2003/0144742 A1 | 7/2003 | King et al. |
| 2003/0162864 A1 | 8/2003 | Pearson et al. |
| 2003/0174576 A1 | 9/2003 | Tague et al. |
| 2003/0181963 A1 | 9/2003 | Pellegrino et al. |
| 2003/0185093 A1 | 10/2003 | Vendrely et al. |
| 2003/0220414 A1 | 11/2003 | Axen et al. |
| 2003/0225364 A1 | 12/2003 | Kraft et al. |
| 2003/0231545 A1 | 12/2003 | Seaton et al. |
| 2004/0010263 A1 | 1/2004 | Boucher et al. |
| 2004/0029996 A1 | 2/2004 | Kuhn |
| 2004/0054377 A1 | 3/2004 | Foster et al. |
| 2004/0059283 A1 | 3/2004 | Kirwan et al. |
| 2004/0068264 A1 | 4/2004 | Treace |
| 2004/0073139 A1 | 4/2004 | Hirsch et al. |
| 2004/0080357 A1 | 4/2004 | Chuang et al. |
| 2004/0092946 A1 | 5/2004 | Bagga et al. |
| 2004/0098015 A1 | 5/2004 | Weikel et al. |
| 2004/0106913 A1 | 6/2004 | Eidenschink et al. |
| 2004/0122438 A1 | 6/2004 | Abrams |
| 2004/0132859 A1 | 7/2004 | Puckett, Jr. et al. |
| 2004/0133124 A1 | 7/2004 | Bates et al. |
| 2004/0133211 A1 | 7/2004 | Raskin et al. |
| 2004/0138759 A1 | 7/2004 | Muller et al. |
| 2004/0157952 A1 | 8/2004 | Soffiati et al. |
| 2004/0157954 A1 | 8/2004 | Imai et al. |
| 2004/0167532 A1 | 8/2004 | Olson et al. |
| 2004/0167562 A1 | 8/2004 | Osorio et al. |
| 2004/0167625 A1 | 8/2004 | Beyar et al. |
| 2004/0193171 A1 | 9/2004 | DiMauro et al. |
| 2004/0215202 A1 | 10/2004 | Preissman |
| 2004/0220672 A1 | 11/2004 | Shadduck |
| 2004/0226479 A1 | 11/2004 | Lyles et al. |
| 2004/0229972 A1 | 11/2004 | Klee et al. |
| 2004/0230309 A1 | 11/2004 | DiMauro et al. |
| 2004/0236313 A1 | 11/2004 | Klein |
| 2004/0249015 A1 | 12/2004 | Jia et al. |
| 2004/0249347 A1 | 12/2004 | Miller et al. |
| 2004/0260303 A1 | 12/2004 | Carrison |
| 2004/0260304 A1 | 12/2004 | Faccioli et al. |
| 2004/0267154 A1 | 12/2004 | Sutton et al. |
| 2005/0014273 A1 | 1/2005 | Dahm et al. |
| 2005/0015148 A1 | 1/2005 | Jansen et al. |
| 2005/0025622 A1 | 2/2005 | Djeridane et al. |
| 2005/0058717 A1 | 3/2005 | Yetkinler et al. |
| 2005/0060023 A1 | 3/2005 | Mitchell et al. |
| 2005/0070912 A1 | 3/2005 | Voellmicke |
| 2005/0070914 A1 | 3/2005 | Constantz et al. |
| 2005/0070915 A1 | 3/2005 | Mazzuca et al. |
| 2005/0083782 A1 | 4/2005 | Gronau et al. |
| 2005/0113762 A1 | 5/2005 | Kay et al. |
| 2005/0143827 A1 | 6/2005 | Globerman et al. |
| 2005/0154081 A1 | 7/2005 | Yin et al. |
| 2005/0180806 A1 | 8/2005 | Green et al. |
| 2005/0203206 A1 | 9/2005 | Trieu |
| 2005/0209695 A1 | 9/2005 | de Vries et al. |
| 2005/0216025 A1 | 9/2005 | Chern Lin et al. |
| 2005/0256220 A1 | 11/2005 | Lavergne et al. |
| 2005/0281132 A1 | 12/2005 | Armstrong et al. |
| 2006/0035997 A1 | 2/2006 | Orlowski et al. |
| 2006/0041033 A1 | 2/2006 | Bisig et al. |
| 2006/0052794 A1 | 3/2006 | McGill et al. |
| 2006/0074433 A1 | 4/2006 | McGill et al. |
| 2006/0079905 A1 | 4/2006 | Beyar et al. |
| 2006/0116643 A1 | 6/2006 | Dixon et al. |
| 2006/0116689 A1 | 6/2006 | Albans et al. |
| 2006/0116690 A1 | 6/2006 | Pagano |
| 2006/0122614 A1 | 6/2006 | Truckai et al. |
| 2006/0148923 A1 | 7/2006 | Ashman et al. |
| 2006/0167148 A1 | 7/2006 | Engqvist et al. |
| 2006/0235338 A1 | 10/2006 | Pacheco |
| 2006/0241644 A1 | 10/2006 | Osorio et al. |
| 2006/0264695 A1 | 11/2006 | Viole et al. |
| 2006/0264967 A1 | 11/2006 | Ferreyro et al. |
| 2006/0266372 A1 | 11/2006 | Miller et al. |
| 2006/0271061 A1 | 11/2006 | Beyar et al. |
| 2006/0276819 A1 | 12/2006 | Osorio et al. |
| 2007/0027230 A1 | 2/2007 | Beyar et al. |
| 2007/0032567 A1 | 2/2007 | Beyar et al. |
| 2007/0055266 A1 | 3/2007 | Osorio et al. |
| 2007/0055267 A1 | 3/2007 | Osorio et al. |
| 2007/0055278 A1 | 3/2007 | Osorio et al. |
| 2007/0055280 A1 | 3/2007 | Osorio et al. |
| 2007/0055284 A1 | 3/2007 | Osorio et al. |
| 2007/0055285 A1 | 3/2007 | Osorio et al. |
| 2007/0055300 A1 | 3/2007 | Osorio et al. |
| 2007/0060941 A1 | 3/2007 | Reiley et al. |
| 2007/0118142 A1 | 5/2007 | Krueger et al. |
| 2007/0142842 A1 | 6/2007 | Krueger et al. |
| 2007/0197935 A1 | 8/2007 | Reiley et al. |
| 2007/0198013 A1 | 8/2007 | Foley et al. |
| 2007/0198023 A1 | 8/2007 | Sand et al. |
| 2007/0198024 A1 | 8/2007 | Plishka et al. |
| 2007/0255282 A1 | 11/2007 | Simonton et al. |
| 2007/0282443 A1 | 12/2007 | Globerman et al. |
| 2008/0039856 A1 | 2/2008 | DiMauro et al. |
| 2008/0044374 A1 | 2/2008 | Lavergne et al. |
| 2008/0058827 A1 | 3/2008 | Osorio et al. |
| 2008/0065087 A1 | 3/2008 | Osorio et al. |
| 2008/0065089 A1 | 3/2008 | Osorio et al. |
| 2008/0065137 A1 | 3/2008 | Boucher et al. |
| 2008/0065142 A1 | 3/2008 | Reiley et al. |
| 2008/0065190 A1 | 3/2008 | Osorio et al. |
| 2008/0071283 A1 | 3/2008 | Osorio et al. |
| 2008/0086133 A1 | 4/2008 | Kuslich et al. |
| 2008/0132935 A1 | 6/2008 | Osorio et al. |
| 2008/0140079 A1 | 6/2008 | Osorio et al. |
| 2008/0140084 A1 | 6/2008 | Osorio et al. |
| 2008/0200915 A1 | 8/2008 | Globerman et al. |
| 2008/0212405 A1 | 9/2008 | Globerman et al. |
| 2008/0228192 A1 | 9/2008 | Beyar et al. |
| 2009/0264892 A1 | 10/2009 | Beyar et al. |
| 2009/0264942 A1 | 10/2009 | Beyar et al. |
| 2009/0270872 A1 | 10/2009 | DiMauro et al. |
| 2010/0065154 A1 | 3/2010 | Globerman et al. |
| 2010/0069786 A1 | 3/2010 | Globerman et al. |
| 2010/0152855 A1 | 6/2010 | Kuslich et al. |
| 2010/0168271 A1 | 7/2010 | Beyar et al. |
| 2010/0268231 A1 | 10/2010 | Kuslich et al. |
| 2012/0307586 A1 | 12/2012 | Globerman et al. |
| 2013/0123791 A1 | 5/2013 | Beyar et al. |
| 2013/0261217 A1 | 10/2013 | Beyar et al. |
| 2013/0345708 A1 | 12/2013 | Beyar et al. |
| 2014/0148866 A1 | 5/2014 | Globerman et al. |

FOREIGN PATENT DOCUMENTS

| | | |
|---|---|---|
| DE | 136018 C | 11/1902 |
| DE | 226956 C | 3/1909 |
| DE | 868497 C | 2/1953 |
| DE | 1283448 B | 11/1968 |
| DE | 1810799 A1 | 6/1970 |

(56) References Cited

FOREIGN PATENT DOCUMENTS

| | | |
|---|---|---|
| DE | 2821785 A1 | 11/1979 |
| DE | 3003947 A1 | 8/1980 |
| DE | 2947875 A1 | 6/1981 |
| DE | 3443167 A1 | 6/1986 |
| DE | 8716073 U1 | 2/1988 |
| DE | 3730298 A1 | 3/1988 |
| DE | 3817101 A1 | 11/1989 |
| DE | 4016135 A1 | 11/1990 |
| DE | 4104092 A1 | 8/1991 |
| DE | 293485 A5 | 9/1991 |
| DE | 19612276 A1 | 10/1997 |
| DE | 10258140 A1 | 7/2004 |
| EP | 0 044 877 A1 | 2/1982 |
| EP | 0 177 781 A1 | 4/1986 |
| EP | 0 235 905 B1 | 12/1990 |
| EP | 0 423 916 A1 | 4/1991 |
| EP | 0 301 759 B1 | 12/1991 |
| EP | 0 475 077 A2 | 3/1992 |
| EP | 0 242 672 B1 | 10/1992 |
| EP | 0 190 504 B1 | 4/1993 |
| EP | 0 425 200 B1 | 8/1994 |
| EP | 0 614 653 A2 | 9/1994 |
| EP | 0 511 868 B1 | 9/1996 |
| EP | 0 748 615 A1 | 12/1996 |
| EP | 0 493 789 B1 | 3/1997 |
| EP | 0 763 348 A2 | 3/1997 |
| EP | 0 669 100 B1 | 11/1998 |
| EP | 1 095 667 A2 | 5/2001 |
| EP | 1 103 237 A2 | 5/2001 |
| EP | 1 104 260 A1 | 6/2001 |
| EP | 1 148 850 A1 | 10/2001 |
| EP | 0 581 387 B1 | 11/2001 |
| EP | 1 247 454 A1 | 10/2002 |
| EP | 1 074 231 B1 | 4/2003 |
| EP | 1 464 292 A1 | 10/2004 |
| EP | 1 552 797 A2 | 7/2005 |
| EP | 1 570 873 A1 | 9/2005 |
| EP | 1 598 015 A1 | 11/2005 |
| EP | 1 829 518 A1 | 9/2007 |
| EP | 1 886 647 A1 | 2/2008 |
| FR | 1548575 A | 12/1968 |
| FR | 2606282 A1 | 5/1988 |
| FR | 2629337 A1 | 10/1989 |
| FR | 2638972 A1 | 5/1990 |
| FR | 2674119 A1 | 9/1992 |
| FR | 2690332 A1 | 10/1993 |
| FR | 2712486 A1 | 5/1995 |
| FR | 2722679 A1 | 1/1996 |
| GB | 8331 A | 0/1905 |
| GB | 179502045 A | 0/1795 |
| GB | 190720207 A | 0/1908 |
| GB | 408668 A | 4/1934 |
| GB | 486638 A | 6/1938 |
| GB | 2114005 A | 8/1983 |
| GB | 2156824 A | 10/1985 |
| GB | 2197691 A | 5/1988 |
| GB | 2268068 A | 1/1994 |
| GB | 2276560 A | 10/1994 |
| GB | 2411849 A | 9/2005 |
| GB | 2413280 B | 3/2006 |
| GB | 2469749 A | 10/2010 |
| JP | 51-134465 A | 11/1976 |
| JP | 54-009110 A | 1/1979 |
| JP | 55-009242 U | 1/1980 |
| JP | 55-109440 A | 8/1980 |
| JP | 62-068893 A | 3/1987 |
| JP | 63-194722 A | 8/1988 |
| JP | 02-122017 A | 5/1990 |
| JP | 02-166235 A | 6/1990 |
| JP | 02-125730 U | 10/1990 |
| JP | 04-329956 A | 11/1992 |
| JP | 07-000410 A | 1/1995 |
| JP | 08-322848 A | 12/1996 |
| JP | 10-146559 A | 6/1998 |
| JP | 10-511569 A | 11/1998 |
| JP | 2001-514922 A | 9/2001 |
| JP | 2004-016707 A | 1/2004 |
| JP | 2005-500103 A | 1/2005 |
| JP | 2008-055367 A | 3/2008 |
| RO | 116784 B1 | 6/2001 |
| RU | 1011119 A | 4/1983 |
| RU | 1049050 A | 10/1983 |
| SU | 662082 A1 | 5/1979 |
| WO | 90/00037 A1 | 1/1990 |
| WO | 92/14423 A1 | 9/1992 |
| WO | 94/12112 A1 | 6/1994 |
| WO | 95/13862 A1 | 5/1995 |
| WO | 96/11643 A1 | 4/1996 |
| WO | 96/19940 A1 | 7/1996 |
| WO | 96/32899 A1 | 10/1996 |
| WO | 96/37170 A1 | 11/1996 |
| WO | 97/18769 A1 | 5/1997 |
| WO | 97/28835 A1 | 8/1997 |
| WO | 98/28035 A1 | 7/1998 |
| WO | 98/38918 A1 | 9/1998 |
| WO | 99/18866 A1 | 4/1999 |
| WO | 99/18894 A1 | 4/1999 |
| WO | 99/29253 A1 | 6/1999 |
| WO | 99/37212 A1 | 7/1999 |
| WO | 99/39661 A2 | 8/1999 |
| WO | 99/49819 A1 | 10/1999 |
| WO | 99/52446 A2 | 10/1999 |
| WO | 00/06216 A1 | 2/2000 |
| WO | 00/44319 A1 | 8/2000 |
| WO | 00/44321 A2 | 8/2000 |
| WO | 00/44946 A1 | 8/2000 |
| WO | 00/54705 A1 | 9/2000 |
| WO | 00/56254 A1 | 9/2000 |
| WO | 01/08571 A1 | 2/2001 |
| WO | 01/13822 A1 | 3/2001 |
| WO | 01/54598 A1 | 8/2001 |
| WO | 01/56514 A1 | 8/2001 |
| WO | 01/60270 A1 | 8/2001 |
| WO | 01/76514 A2 | 10/2001 |
| WO | 02/00143 A1 | 1/2002 |
| WO | 02/02033 A1 | 1/2002 |
| WO | 02/19933 A1 | 3/2002 |
| WO | 02/064062 A2 | 8/2002 |
| WO | 02/064194 A1 | 8/2002 |
| WO | 02/072156 A2 | 9/2002 |
| WO | 02/096474 A1 | 12/2002 |
| WO | 03/007854 A1 | 1/2003 |
| WO | 03/015845 A2 | 2/2003 |
| WO | 03/022165 A1 | 3/2003 |
| WO | 03/061495 A2 | 7/2003 |
| WO | 03/078041 A1 | 9/2003 |
| WO | 03/101596 A1 | 12/2003 |
| WO | 2004/002375 A1 | 1/2004 |
| WO | 2004/019810 A2 | 3/2004 |
| WO | 2004/071543 A1 | 8/2004 |
| WO | 2004/075965 A1 | 9/2004 |
| WO | 2004/080357 A1 | 9/2004 |
| WO | 2004/110300 A2 | 12/2004 |
| WO | 2005/000138 A1 | 1/2005 |
| WO | 2005/017000 A1 | 2/2005 |
| WO | 2004/110292 A3 | 3/2005 |
| WO | 2005/032326 A2 | 4/2005 |
| WO | 2005/048867 A2 | 6/2005 |
| WO | 2005/051212 A1 | 6/2005 |
| WO | 2005/110259 A1 | 11/2005 |
| WO | 2006/011152 A2 | 2/2006 |
| WO | 2006/039159 A1 | 4/2006 |
| WO | 2006/062939 A2 | 6/2006 |
| WO | 2006/090379 A2 | 8/2006 |
| WO | 2007/015202 A2 | 2/2007 |
| WO | 2007/036815 A2 | 4/2007 |
| WO | 2007/148336 A2 | 12/2007 |
| WO | 2008/004229 A2 | 1/2008 |
| WO | 2008/032322 A2 | 3/2008 |
| WO | 2008/047371 A2 | 4/2008 |

OTHER PUBLICATIONS

Gangi, A., "Percutaneous Vertebroplasty Guided by a Combination of CT and Fluoroscopy," AJNR 15:83-86 (1994).

(56) References Cited

OTHER PUBLICATIONS

Gangi, A., "CT-Guided Interventional Procedures for Pain Management in the Lumbosacral Spine," Radiographics 18:621-33 (1998).
Gangi, A., "Computed Tomography CT and Fluoroscopy-Guided Vertebroplasty: Results and Complications in 187 Patients," Seminars in Interventional Radiology 16(2):137-42 (1999).
Garfin, S. R. et al., "New Technologies in Spine, Kyphoplasty and Vertebroplasty for the Treatment of Painful Osteoporotic Compression Fractures," Spine 26(14:1511-15 (2001).
Gheduzzi, S. et al., "Mechanical Characterisation of Three Percutaneous Vertebroplasty Biomaterials," J. Mater Sci Mater Med 17(5):421-26 (2006).
Giannitsios, D. et al., "High Cement Viscosity Reduces Leakage Risk in Vertebroplasty," European Cells & Mat. 10 supp. 3:54 (2005).
Grados F. et al.,"Long-Term Observations of Vertebral Osteoporotic Fractures Treated by Percutaneous Vertebroplasty," Rheumatology 39:1410-14 (2000).
Greenberg, "Filling Root Canals in Deciduous Teeth by an Injection Technique," Dental Digest 574-575 (Dec. 1961).
Greenberg, "Filling Root Canals by an Injection Technique," Dental Digest 61-63 (Feb. 1963).
Greig, D., "A New Syringe for Injecting Paraffin," The Lancet 611-12 (Aug. 29, 1903).
Hasenwinkel, J. et al., "A Novel High-Viscosity, Two-Solution Acrylic Bone Cement: Effect of Chemical Composition on Properties," J. Biomed. Materials Research 47(1):36-45 (1999).
Hasenwinkel, J. et al., "Effect of Initiation Chemistry on the Fracture Toughness, Fatigue Strength, and Residual Monomer Content of a Novel High-Viscosity, Two-Solution Acrylic Bone Cement," J. Biomed. Materials Res. 59 (3):411-21 (2001).
Heini, P., "Percutaneous Transpedicular Vertebroplasty with PMMA: Operative Technique and Early Results," EUR Spine J. v. 9, pp. 445-450, Springer-Verlag (2000).
Heini, P. et al., "Augmentation of Mechanical Properties in Osteoporatic Vertebral Bones—a Biomechanical Investigation of Vertebroplasty Efficacy With Different Bone Cements," EUR Spine J. v. 10, pp. 164-171, Springer-Verlag (2001).
Heini et al., "The Use of a Side-Opening Injection Cannula in Vertebroplasty," Spine 27(1):105-09 (2002).
Hernandez et al., "Influence of Powder Particle Size Distribution on Complex Viscosity and Other Properties of Acrylic Bone Cement for Vertebroplasty and Kyphoplasty," J. Biomed. Mat. Res. 77B:98-103 (2006).
Hide, I. et al., "Percutaneous Vertebroplasty: History, Technique and current Perspectives," Clin. Radiology 59:461-67 (2004).
Hu, M. et al., "Kyphoplasty for Vertebral Compression Fracture Via a Uni-Pedicular Approach," Pain Phys. 8:363-67 (2005).
International Search Report, from PCT/IB06/052612, mailed Oct. 2, 2007.
International Preliminary Report on Patentability, from PCT/IB06/053014, dated Apr. 10, 2008.
International Search Report, from PCT/IL05/00812, mailed Feb. 28, 2007.
International Search Report, from PCT/IL06/00239, mailed Jan. 26, 2007.
International Search Report, from PCT/IL07/00484, mailed Apr. 17, 2008.
International Search Report, for PCT/IL07/00808, issued Aug. 22, 2008 (2 Pages).
International Search Report, from PCT/IL07,00833, mailed Apr. 4, 2008.
International Search Report, from corresponding PCT/IL07/01257, dated Jul. 15, 2008 (1 Page).
International Search Report, for PCT/MX03/000027, filed Mar. 14, 2003.
Ishikawa et al., "Effects of Neutral Sodium Hydrogen Phosphate on Setting Reaction and Mechanical Strength of Hydroxyapatite Putty," J. Biomed. Mat. Res. 44:322-29 (1999).
Ishikawa et al., "Non-Decay Type Fast-Setting Calcium Phosphate Cement: Hydroxyapatite Putty Containing an Increased Amount of Sodium Alginate," J. Biomed. Mat. Res. 36:393-99 (1997).
Japanese Office Action issued Apr. 9, 2013 for Application No. 2007-556708.
Japanese Office Action issued Dec. 6, 2011 for Application No. 2008-524651 (9 Pages).
JP Office Action, from JP Appl No. 2008-532910, mailed Jul. 19, 2011 (3 Pages).
Japanese Office Action for Application No. 2009-516062, dated Oct. 16, 2012 (6 pages).
Japanese Interrogation for Application No. 2009-516062 (Appeal No. 2013-002371) issued Jul. 9, 2013 (9 Pages).
Japanese Office Action for Application No. 2009-517607, dated Aug. 9, 2011. (10 pages).
Japanese Office Action for Application No. 2009-517607, dated Aug. 28, 2012. (4 pages).
Japanese Office Action for Application No. 2009-517607, dated Aug. 27, 2013. (6 pages).
Jasper, L.E. et al., "The Effect of Monomer-to-Powder Ratio on the Material Properties of Cranioplastic," Bone 25 (2):27S-29S (1999).
Jensen, Mary E. et al., "Percutaneous Polymethylmethacrylate Vertebroplasty in the Treatment of Osteoporotic Vertebral Body Compression Fractures: Technical Aspects," AJNR 18:1897-1904 (1997).
Jensen, Mary E. et al., "Percutaneous Vertebroplasty in the Treatment of Osteoporotic Compression Fractures," Spine Interventions 10(3):547-568 (2000).
Juneja, BL, Plastic Deformation of Metals and Related Properties. Chapter 1. New Age International. p. 1-29, 2010.
Kallmes, D. et al., "Radiation Dose to the Operator During Vertebroplasty: Prospective Comparison of the Use of 1-cc Syringes Versus an Injection Device," AJNR Am. J. Neuroradiol. 24:1257-60 (2003).
Kaufmann et al, "Age of Fracture and Clinical Outcomes of Percutaneous Vertebroplasty," Am. J. Neuroradiology 22:1860-63 (2001).
Krause et al., "The Viscosity of Acrylic Bone Cements," J. Biomed. Mat. Res. 16:219-43 (1982).
Kuehn, Klaus-Dieter, Bone Cements—Uptodate Comparison of Physical and Chemical Properties of Commercial Materials, Springer-Verlag Heidelberg Germany p. 7-8, 17, 38 (2000).
Kuehn et al., Acrylic bone cements: composition and properties. Orthop Clin North Am. Jan. 2005;36(1):17-28, v.
Lake, R., "The Restoration of the Inferior Turbinate Body by Paraffin Injections in the Treatment of Atrophic Rhinitis," The Lancet 168-69 (Jan. 17, 1903).
Lewis, "Properties of Acrylic Bone Cement: State of the Art Review," J. Biomed. Mat. Res. Appl. Biomaterials 38 (2):155-82 (p. 158 s.Viscosity) (1997).
Lewis, "Toward Standardization of Methods of Determination of Fracture Properties of Acrylic Bone Cement and Statistical Analysis of Test Results," J. Biomed. Research: Appl. Biomaterials 53(6):748-68 (2000).
Japanese Office Action for Application No. 2009-517607, dated Feb. 4, 2014. (8 pages).
[No Author] Glasgow Medico-Chirurgical Society, The lancet 1364 (May 18, 1907).
[No Author] Heraeus Palacos R, 2008, Palacos R, High Viscosity Bone Cement.
[No Author Listed] The CEMVAC Method, Johnson & Johnson Orthopaedics, Raynhann, MA. Date Unknown, 2 pages.
[No Author] Kyphom Medical Professionals, KyphXProducts (Nov. 8, 2001).
[No Author] Medsafe Palacos R 2007, Data Sheet : Palacos R Bone cement with Garamycin pp. 1-7; http://www.medsafe.govt.nz/profs/datasheet/p/palacosbonecements.htm.
[No Author] Parallax Medical, Inc., Exflow Cement Delivery System (May 16, 2000).
Al-Assir, et al., "Percutaneous Vertebroplasty: A Special Syringe for Cement Injection," AJNR Am. J. Neuroradiol. 21:159-61 (Jan. 2000).

(56) References Cited

OTHER PUBLICATIONS

Amar, Arun P. et al., "Percutaneous Transpedicular Polymethylmethacrylate Vertebroplasty for the Treatment of Spinal Compression Fractures," Neurosurgery 49(5):1105-15 (2001).
Andersen, M. et al., "Vertebroplastik, ny behandling af osteoporotiske columnafrakturer?", Ugeskr Laeger 166/6:463-66 (Feb. 2, 2004) [English Abstract Only].
Australian Office Action issued Mar. 7, 2013 for Application No. 2012203300 (6 pages).
Avalione & Baumeister III, Marks' Standard Handbook for Mechanical Engineers, 10 ed, pp. 5-6 (1996).
Baroud, G., "Influence of Mixing Method on the Cement Temperature-Mixing Time History and Doughing Time of Three Acrylic Cements for Vertebroplasty," J Biomed Mater Res Part B: Appl Biomater, 68B, 112-116 (2003).
Baroud et al., "Injection Biomechanics of Bone Cements Used in Vertebroplasty," Biomed. Mat. & Eng. 00:1-18 (2004).
Barr, J.D., "Percutaneous Vertebroplasty for pain Relief and Spinal Stabilization," Spine 25(8):923-28 (2000).
Belkoff, S.M. et al., "An In Vitro Biomechanical Evaluation of Bone Cements Used in Percutaneous Vertebroplasty, " Bone 25(2):23S-26S (1999).
Belkoff, S. et al., The Biomechanics of Vertebroplasty, the Effect of Cement Volume on Mechanical Behavior, SPINE 26(14):1537-41 (2001).
Belkoff, S.M. et al., "An Ex Vivo Biomechanical Evaluation of a Hydroxyapatite Cement for Use with Kyphoplasty," Am. J. Neurorad. 22:1212-16 (2001).
Belkoff, S.M. et al., "An Ex Vivo Biomechanical Evaluation of a Inflatable Bone Tamp Used in the Treatment of Compression Fracture," SPINE 26(2):151-56 (2001).
Blinc, A et al., "Methyl-methacrylate bone cement surface does not promote platelet aggregation or plasma coagulation in vitro," Thrombosis Research 114:179-84 (2004).
Bohner, M. et al., "Theoretical and Experimental Model to Describe the Injection of a Polymethacrylate Cement into a Porous Structure," Biomaterials 24(16):2721-30 (2003).
Breusch, S. et al., "Knochenzemente auf Basis von Polymethylmethacrylat," Orthopade 32:41-50 (2003) w/ abs.
Canale et al., "Campbell's operative orthopaedic—vol. 3—ninth ed", Mosby:P2097,2121,2184-85,2890-96, (1998) abstracts.
Carrodegus et al., "Injectable Acrylic Bone Cements for Vertebroplasty with Improved Properties," J. Biomed. Materials Res. 68(1):94-104 (Jan. 2004).
Codman & Shurtleff, "V-MAX™ Mixing and Delivery Device," Catalog No. 43-1056 (2001).
Cole et al., "AIM Titanium Humeral Nail System," Surgical Technique. DePuy Orthopaedics 17P (2000).
Combs, S. et al., "The Effects of Barium Sulfate on the Polymerization Temperature and Shear Strength of Surgical Simplex P," Clin. Ortho. and Related Res. pp. 287-291 (Jun. 4, 1979).
Cotton, A. et al., "Percutaneous Vertebroplasty: State of the Art," Scientific Exhibit, Radiographics 18:311-20 (1998).
Cromer, A., "Fluids," Physics for the Life Sciences, 2:136-37 (Jan. 1977).
Dean, J.R. et al., "The Strengthening Effect of Percutaneous Vertebroplasty," Clin Radiol. 55:471-76 (2000).
Deramond, H. et al, "Percutaneous Vertebroplasty with Polymethylmethacrylate, Technique Indications and Results," Radiologic Clinics of North America 36(3) (May 1988).
Deramond, H. et al., "Temperature Elevation Caused by Bone cement Polymerization During Vertbroplasty," Bone 25 (2):17S-21S (1999).
DeWijn, J.R., Characterization of Bone Cements, The Institute of Dental Materials Science and Technology and the Dept of Ortho., Catholic University, Netherlands 46:38-51 (1975).
Edeland, "Some additional suggestions for an intervertebral disc prothesis," J. Biomed. Eng. XP008072822, 7 (1):57-62 (1985.
European Search Report, from EP05763930.4; mailed Sep. 11, 2008.
Supp. EP Search Report, from EP Appl. No. 05763930.4, dated Sep. 11, 2008.
Supp. EP Search Report, from EP Appl. No. 06711221.9, dated Sep. 15, 2008.
European Search Report, from EP06780252.0, mailed Oct. 29, 2009.
Supp. EP Search Report, from EP 07766838.2, dated May 18, 2011 (2 Pages).
Supp. EP Search Report, from EP Appl. No. 07766863.0, dated Apr. 12, 2011 (2 Pages).
European Search Report, from EP07827231.7, mailed Sep. 12, 2011 (9 Pages).
European Search Report, from EP09151379.6, mailed Oct. 20, 2009.
European Search Report, from EP10182693.1, mailed Mar. 2, 2011 (3 Pages).
European Search Report, from EP10182769.9, mailed Mar. 2, 2011 (3 Pages).
European Search Report, from EP10192300.1, mailed Mar. 24, 2011 (3 Pages).
European Search Report, from EP10192301.9, mailed Mar. 24, 2011 (3 Pages).
European Search Report, from EP10192302.7, mailed Mar. 24, 2011 (3 Pages).
European Search Report for Application No. 12181745.6, issued Sep. 25, 2012. (9 pages).
European Search Report for Application No. 13174874.1, issued Nov. 13, 2013 (6 pages).
Farrar, D.F. et al., "Rheological Properties of PMMA Bone Cements During Curing," Biomaterials 22:3005-13 (2001).
Feldmann, H., [History of injections. Pictures from the history of otorhinolaryngology highlighted by exhibits of the German History of Medicine Museum in Ingolstadt]. Laryngorhinootologie. Apr. 2000;79(4):239-46. [English Abstract Only].
Lewis, G. et al., "Rheological Properties of Acrylic Bone Cement During Curing and the Role of the Size of the Powder Particles," J. Biomed. Mat. Res. Appl. Biomat. 63(2):191-99 (2002).
Li, C. et al., "Thermal Characterization of PMMA-Based Bone Cement Curing," J. Materials Sci.: Materials in Medicine 15:84-89 (2004).
Liang, B. et al., "Preliminary Clinical Application of Percutaneous Vertebroplasty," Zhong Nan Da Xue Bao Yi Xue Ban 31(1):114-9 (2006)(abs. only).
Lieberman, I.H. et al., "Initial Outcome and Ethciacy of Kyphoplasty in the Treatment of Painful Osteoporatic Vertebral Compression Fractures," Spine 26(14:1631-38 (2001).
Lindeburg, M., "External Pressurized Liquids," Mechanical Eng. Ref. Manual for the PE Exam, 10:14-15(May 1997).
Lu Orthopedic Bone Cement. Biomechanics and Biomaterials in Orthopedics. Ed. Poitout London: Springer-Verlag London Limited Jul. 2004 86-88.
Mathis, John et al., "Percutaneous Vertebroplasty: A Developing Standard of Care for Vertebral Compression Fractures," AJNR Am. J. Neurorad. 22:373-81 (2001).
Marks' Standard Handbook for Mechanical Engineers, Section 5.1 Mechanical properties of materials. Written by John Symonds, pp. 5-1 to 5-6 (Tenth ed. 1996), 11 pages.
Mendizabal et al., Modeling of the curing kinetics of an acrylic bone cement modified with hydroxyapatite. International Journal of Polymeric Materials. 2003;52:927-938.
Morejon et al., Kinetic effect of hydroxyapatite types on the polymerization of acrylic bone cements. International Journal of Polymeric Materials. 2003;52(7):637-654.
Moura, W.F. et al., "Biological and Mechanical Properties of PMMA-Based Bioactive Bone Cements," Biomaterials 21:2137-46 (2000).
Noetzel, J. et al., Calcium Phosphate Cements in Medicine and Dentistry—A Review of Literature, Schweiz Monatsschr Zehmed 115(12):1148-56 (2005). German language article, English abstract only.
Nussbaum et al., "The Chemistry of Acrylic Bone Cements and Implications for Clinical Use in Image-Guided Therapy," J. Vasc. Interv. Radiol. 15:121-26 (2004).
O'Brien, J. et al., "Vertebroplasty in patients with Severe Vertebral Compression Fractures: A Technical Report," AJNR 21:1555-58 (2000).
Odian, G., "Principles of Polymerization," 3rd Edition, pp. 20-23, Feb. 9, 2004, John Wiley & Sons, New York (6 Pages).

(56) References Cited

OTHER PUBLICATIONS

Padovani, B. et al., "Pulmonary Embolism Caused by Acrylic Cement: A Rare Complication of Percutaneous Vertebroplasty," AJNR 20:375-77 (1999).

Paget, S., "The Uses of Paraffin in Plastic Surgery," The Lancet 1354 (May 16, 1903).

Pascual, B. et al., "New Aspects of the Effect of Size and Size Distribution on the Setting Parameters and Mechanical Properties of Acrylic Bone Cements," Biomaterials 17(5):509-16 (1996).

Rimnac, CM, et al., "The effect of centrifugation on the fracture properties of acrylic bone cements," JB&JS 68A (2):281-87 (1986).

Robinson, R. et al., "Mechanical Properties of Poly(methyl methacrylate) Bone Cement," J. Biomed. Materials Res. 15(2):203-08 (2004).

Ryu, K. S. et al., "Dose-Dependent Epidural Leakage of Polymethylmethacrylate after Percutaneous Vertebroplasty in Patients with Osteoporotic Vertebral Compression Fractures," J. Neuro: Spine 96:56-61 (2002).

Saha, S. et a., "Mechanical Properties of Bone Cement: A Review," J. Biomed. Materials Res. 18(4):435-62 (1984).

Serbetci, K. et al., "Thermal and Mechanical Properties of Hydroxyapatite Impregnated Acrylic Bone Cements," Polymer Testing 23:145-55 (2004).

Shah, T., Radiopaque Polymer Formulations for Medical Devices; Medical Plastics and Biomaterials Special Section; Medical device & Diagnostic Industry pp. 102-111 (2000).

Sreeja et al., Studies on poly(methyl methacrylate)/polystyrene copolymers for potential bone cement applications. Metals Materials and Processes. 1996;8(4):315-322.

Steen, "Laser Surface Treatment," Laser Mat. Processing, Springer 2d ed. ch. 6:218-71 (2003).

Varela et al., "Closed Intramedullary Pinning of Metacarpal and Phalanx Fractures," Orthopaedics 13(2):213-15 (1990).

Vasconcelos, C., "Transient Arterial Hypotension Induced by Polymethyacrylated Injection During Percutaneous Vertebroplasty," Letter to the Editor, JVIR (Aug. 2001).

Walton, A, "Some Cases of Bone Cavities Treated by Stopping With Paraffin," The Lancet 155 (Jan. 18, 1908).

Weissman et al., "Trochanteric Fractures of the Femur Treatment with a Strong Nail and Early Weight-Bearing," Clin. Ortho. & Related Res. 67:143-50 (1969).

Wimhurst, J.A., et al., "The Effects of Particulate Bone Cements at the Bone-Implant Interface," J. Bone & Joint Surgery pp. 588-592 (2001).

Wimhurst, J.A. et al., "Inflammatory Responses of Human Primary Macrophages to Particulate Bone Cements in Vitro," J. Bone & Joint Surgery 83B:278-82 (2001).

Yang et al., Polymerization of acrylic bone cement investigated by differential scanning calorimetry: Effects of heating rate and TCP content. Polymer Engineering and Science. Jul. 1997;1182-1187.

Zapalowicz, K. et al., "Percutaneous Vertebroplasty with Bone Cement in the Treatment of Osteoporotic Vertebral Compression Fractures," Ortopedia Traumatologia Rehabilitacja NR Jan. 2003.

\* cited by examiner

US 8,992,541 B2

HYDRAULIC DEVICE FOR THE INJECTION OF BONE CEMENT IN PERCUTANEOUS VERTEBROPLASTY

CROSS-REFERENCE TO RELATED APPLICATIONS

This application is a continuation of U.S. application Ser. No. 10/549,409, filed Sep. 14, 2005, which is the U.S. National Phase Application of International Application No. PCT/MX2003/000027 filed Mar. 14, 2003, each application of which are incorporated herein by reference.

TECHNICAL FIELD

This invention in a general way relates to the medical area in procedures where it is required to inject a dense or viscous fluid through a needle, in a particular way the viscous material is the polymethylmethacrylate. it is used in procedures like percutaneous vertebroplasty, kyphoplasty or other surgical events of the field. It has applications in other areas where it is required to apply at distance a dense and viscous liquid.

BACKGROUND OF THE INVENTION

Percutaneous vertebroplasty is a minimally invasive interventional radiological procedure that consists on injecting bone cement (Polymethylmethacrylate, PMMA) in the vertebral body, by trans-pedicular or oblique approach through a bone biopsy needle.

It was developed in France in 1984 for the treatment of aggressive or painful haemangiomas of vertebral bodies. For its analgesic effect, its use was quickly extended for the treatment of lytic metastatic lesions or myeloma and mainly in fractures or vertebral collapse due to osteoporosis. The procedure is indicated in those cases that are presented with severe and disabling pain that doesn't respond to conservative measures such as: corset use, analgesic and anti-inflammatory treatment or bed rest.

Most of the patients with this suffering are between the 6th and 8th decade of life. In this group of advanced age, the immobilization resulting from vertebral fractures has severe consequences in their general medical conditions, it predisposes them to cardiopulmonary, intestinal, circulatory complications, etc. Besides pain, the psychological effects can be devastating, it deteriorates the quality and reduces the expectation of life.

Vertebroplasty is a procedure that is carried out in hospital facilities that requires specialized medical personnel. It is performed in a hemodinamia room or cath lab, and it requires of the use of radiological equipment with high resolution fluoroscopy, mounted in a C arm. Currently, this injection is carried out in a manual and direct way and the operator is exposed to ionizing radiation every time that he/she practices a vertebroplasty. The injection of bone cement is made with fluoroscopic control, connecting an insulin syringe to the needle. This implies that the surgeon is in direct contact with the patient and therefore, overexposed to primary or secondary ionizing radiation during the lapse of the procedure of the vertebroplasty.

The primary radiation is the X ray beam coming from the X ray tube and received by the patient in a direct way, The secondary radiation it the one resulting on the deviation of the primary beam in the patient's body tissues and doesn't contribute to the formation of a diagnostic image, it is spread in all directions and it is the main source of exposure of medical personnel.

The insulin syringe is used since a small diameter barrel is required to have less resistance for the manual injection of high viscosity bone cement, each syringe is filled approximately in half or two thirds of its capacity to avoid bending or breaking the plunger when exercising the required injecting pressure that may be considerable. The volume needed to obtain the expected results varies from 3 ml up to 9 ml, therefore, 5 to 18 syringe exchanges are necessary, this favors the solidification of the polymethylmethacrylate and it can prevent to inject the wanted quantity.

If larger diameter syringes are used, the manual pressure is insufficient due to the density and viscosity of the bone cement; and becomes necessary the employment of a mechanical device to be able to exercise the required pressure. At the state of the art, there are commercially available devices such as pressure gun type or threaded plunger mechanisms connected directly to the needle that deposits the cement in the bone or through a high pressure short tube. The use of a long tube would have considerable resistance to the flow of the cement, favoring its solidification.

In most of these devices the syringe is not interchangeable, it is loaded with the total volume to inject and therefore, are of larger diameter and the increased resistance to the flow of the cement becomes worse with time due to solidification of cement.

On the other hand, the conventional hypodermic syringes are not designed for high pressure injection, the plunger and the fingers supporting wings bend easily.

The devices of the previous technique solve only the mechanical problem of injecting the dense and viscous cement through the needle but they are focused on exercising the necessary pressure directly on the patient or at a very short distance of the radiation source. They don't allow the operator to maintain an appropriate distance to reduced exposure to secondary radiation at acceptable levels according with the international radiological protection norms.

On the other hand, some mechanical devices do not allow control or manual sensibility of the exercised pressure and speed of the injection of the cement, important factors in the prevention of undesirable leaks and complications. Some devices that apply cement in the current state of the art are for example:

The patent application of the United States of America No. 2003/0018339, for Higueras et al, published Jan. 23, 2003, it discloses an application device for the controlled injection of hone cement, mounted in a syringe loaded with the cement, as a cartridge, which is discharged by a threaded metallic plunger placed in the other end of the device, it is useful for controlling the pressure exercised on the plunger of the syringe but it is a short device in which the operator is near the patient; It also contains the total load of cement.

On the other hand, due to the viscosity of the cement and quantity keeps certain dynamic memory that doesn't allow sudden interruption of the injection.

The patent application of the United States of America No. 2002/0156483, for Voellmicke et al, published Oct. 24, 2002, discloses a vertebroplasty device and bone cement, it contains two compartments, one for mixture of the cement and the other for storage and injection into the bone. This dual camera device for blending and injection, consists of a lodging camera with a plunger moving in an axial way, the cameras are in communication by a check valve that only allows the passage of the cement in one direction. An extra force can be exercise on the plunger by means of a lever that increases the mechanical force and therefore the pressure in the injection camera. This is a device in which it is necessary to work the piston of the blending camera and the piston of the injection camera to empty one and fill the other one alternatively. It is a short device, it is necessary to be near the patient and doesn't reduce the exposure to secondary ionizing radiation.

The patent application of the United States of America No. 2002/0099384, for Scribner et al, published Jul. 25, 2002, discloses a system and method to treat vertebral bodies. It is a special syringe with two concentric plungers. The first camera that has a first transverse section and a second smaller camera than the first one. Both cameras communicate to each other. The first camera includes a gate to receive the material inside the filling instrument, the second camera includes a gate to discharge the contained material. A first plunger suited to pass through the first camera and displace the material. A second plunger to pass through the interior of the first plunger's concentric hole and reach the interior of the second camera to displace the material through the exit in the second camera to inject into the needle toward the interior of the vertebral body. Although this device provides control in the injection of the bone cement, the operator is too near the patient.

In general the injection devices have a bolster that impels the viscous fluid by means of a manual trigger moved by a screw mechanism (inclined plane), there are others that have a gun like body such as the device of the Patent Application of the United States of America. 2002/0049448. for Sand et al, published Apr. 25, 2002, It has a tubular body that stores a viscous flowing material (bone cement), it is a longitudinal body with a providing end and a driving end, a plunger housed inside the tubular body that displaces the flowing material along the longitudinal axis of the tubular body, the driving mechanism has a handle like a gun to hold with a hand, while injecting with the other hand by means of the plunger that advances due the pressure exerted by a threaded mechanism. These mechanisms with big deposits have the inconvenience that the cement can end up solidifying in the conduit at the time of application and impede to apply the total amount of cement inside the affected vertebral body. On the other hand, with the excess of pressure generated by these devices, the cement could leak outside of the vertebral body, since the fluid (PMMA), for its viscosity, possesses a remaining flowing memory that may be difficult to control.

The Patent of the U.S. Pat. No. 6,348,055, for Preissman, published Feb. 19, 2002, protects a bone cement applying device with screw mechanism in which the preparation of the total volume of cement is made, this mechanism has an intermediate stabilizer that avoids the turns of the whole device during the application of pressure to the fluid. The stabilizer is a lever perpendicular to the screw body that can be sustain with a hand, while with the other hand exercises the pressure to inject the cement inside the vertebral body. This device is also operated very near the patient and therefore, the operator is exposed to secondary ionizing radiation. Another inconvenience is that if the cement solidifies in the system and has not reached the vertebral body in the proper amount, it is necessary to make another preparation previous placement of another needle in a different and appropriate position for the new requirement.

The Patent Application of the United States of America No. 2002/0010431, for Dixon et al, published Jan. 24, 2002, discloses a screw device for high pressure with a threaded axis that impels a plunger inside a camera full with viscous bone cement. This device has the inconvenience that one doesn't have manual sensitivity and control of the pressure exercised, it is not easy to exchange the syringes with the bone cement. As a matter of fact, it is the only syringe of the cartridge.

BRIEF SUMMARY OF THE INVENTION

Among the several objects of the present invention, a better control of the pressure in the placement of bone cement or other viscous materials in the bone is provided. The invention facilitates the injection of viscous filler in trabecular bone or a cavity formed in the vertebral body.

Another object of the present invention it is to provide a hydraulic device to treat vertebral fractures and reduce the pain, stabilize the vertebral body, to obtain higher resistance to compression, avoid further collapse and at the same time, to allow early mobilization of the patients and improve their quality of life.

It is still another object of the present invention, to provide a device for the injection of viscous material in the vertebral body that allows the operator to keep and appropriate distance (1.0 m to 1.5 m) in order to reduce exposure to ionizing radiation at acceptable levels within the international norms.

It is also another object of the present invention, to provide a hydraulic press like device using syringes of unequal caliber (3 and 10 ml) to exercise hydraulic pressure at distance transmitted from a proximal, manual syringe of smaller caliber, through the polyethylene tube until the distal or injecting syringe.

It is another object of the present invention to provide a cylinder of pressure with mechanical advantage complementary to an hydraulic system of syringes for injection at distance of polymethylmethacrylate suspension in the cancellous bone of a vertebral body. This way, the overexposure of the operator to ionizing radiation is reduced.

It is still another object of the present invention to provide a hollow cylinder or body of pressure in the shape of an inverted syringe to form a hydraulic device that allows manual control on the volume and velocity of injection polymethylmethacrylate (PMMA) and also immediate interruption of the pressure applied on the fluid.

It is still an object of the present invention, to provide a device that prevents the movements or abnormal displacements of the needle during the injection and syringes exchange (1 or 2 exchanges may be necessary), it reduces time loss and allows to maintain the bone cement loaded syringes in a recipient or cold atmosphere to slow time of solidification.

It is another object of the present invention, to provide a device that uses syringes from 3 to 5 ml that require smaller injection pressure, and can be exchanged easily with a single 90° rotation movement, Hub Lock type.

It is still an object of the present invention, to provide a device for injection of viscous material that can be manufactured of plastic, aluminum or any other disposable light-weighted material for single use or suitable for re-sterilization, sturdy enough to support the pressure of injection.

It is another object of the present invention to provide a flexible hydraulic, light-weighted device that prevents the movements or unwanted displacements of the needle during the injection.

BRIEF DESCRIPTION OF THE DRAWINGS

The FIG. 1, represents the connection outline of the novel hydraulic press like device for injection at distance, of the present invention.

The FIG. 2, represents an injection device with a screw type threaded plunger of the previous technique.

Figure 3:
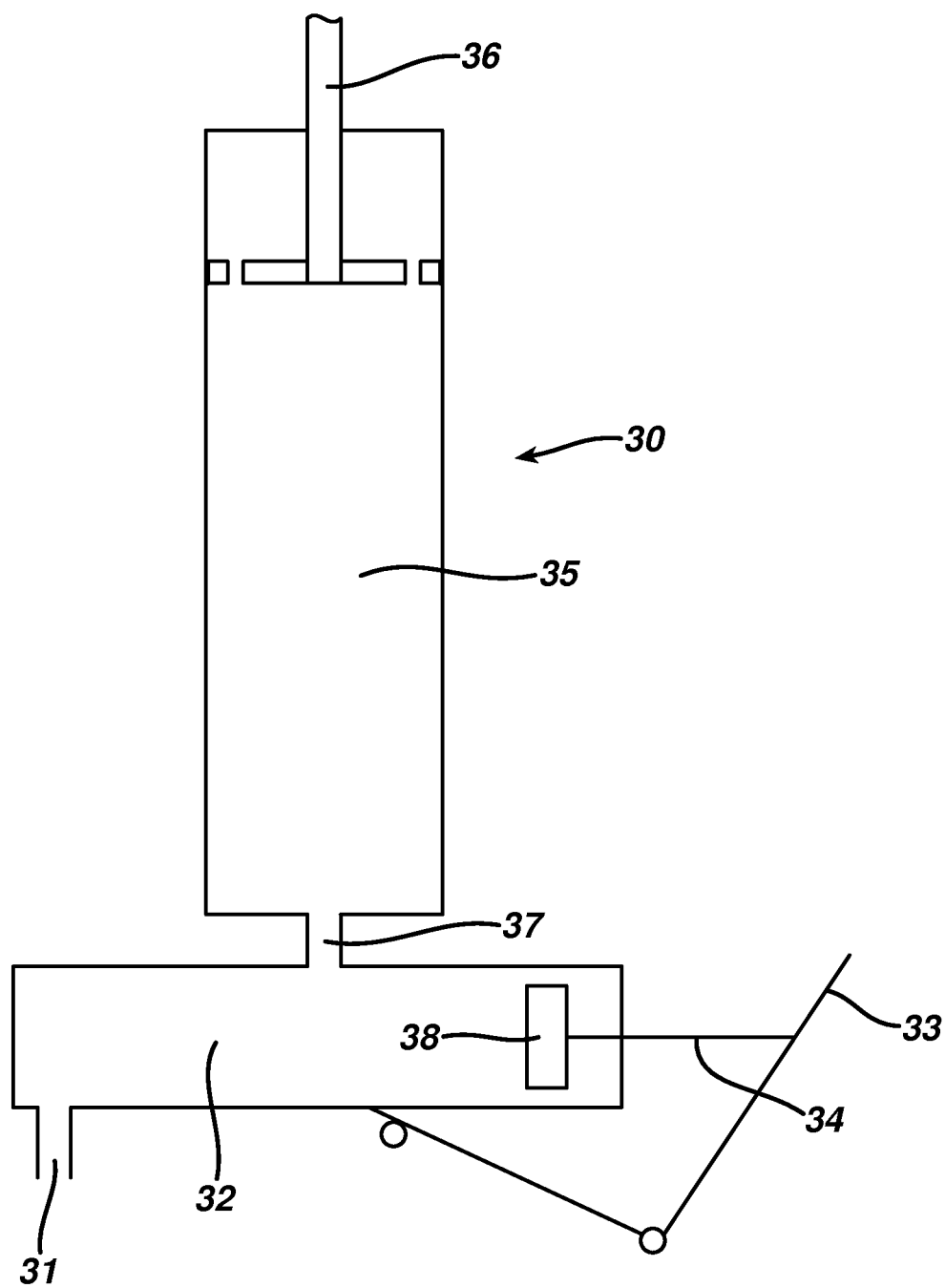
Figure 4:
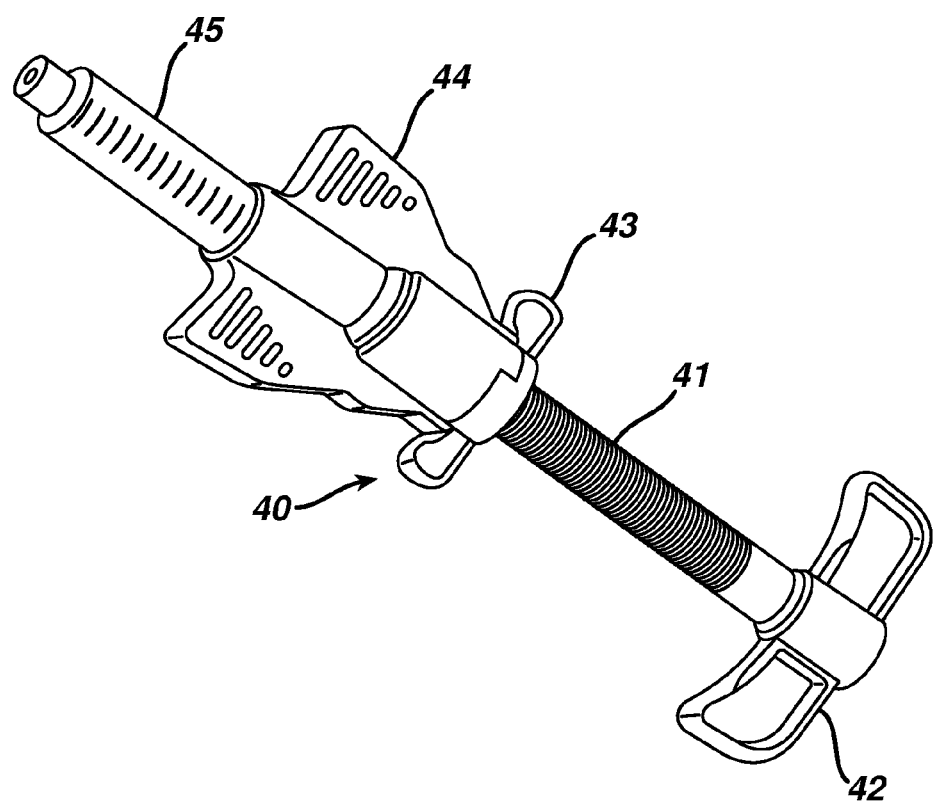

The FIG. 3, represents a device of injection of the previous technique, which has a recipient to make the mixture, another to exercise the injecting pressure. each recipient contains a check valve in their exit holes to avoid re-flow The FIG. 4, represents a device of injection of the previous technique, which contains a larger capacity syringe in which the total amount of bone cement mixture is placed to inject, impelled by a threaded plunger.

Figure 5:
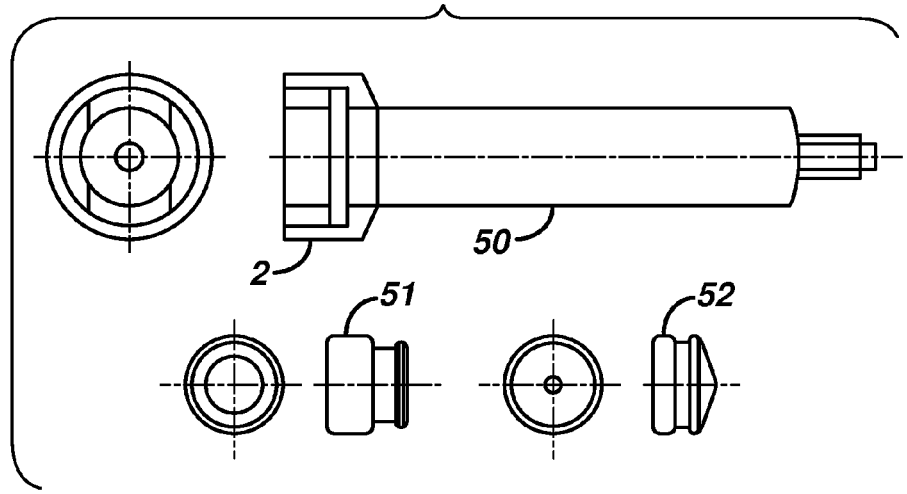

The FIG. 5 represents the device object of the present invention corresponding to the transverse view of the piston together with the rubber cap.

Figure 6:
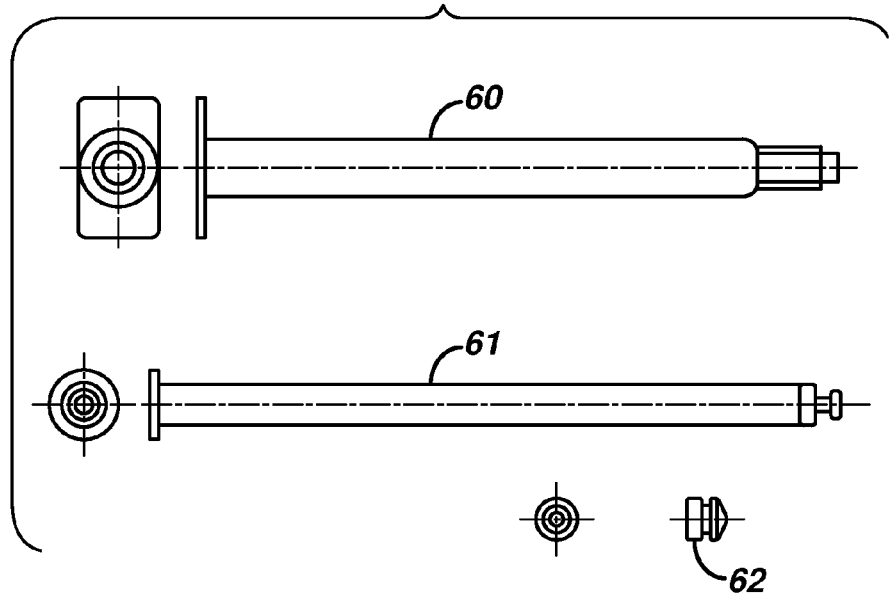

The FIG. 6 represents the smaller, manual syringe for control of the device with the plunger and rubber cap.

Figure 7:
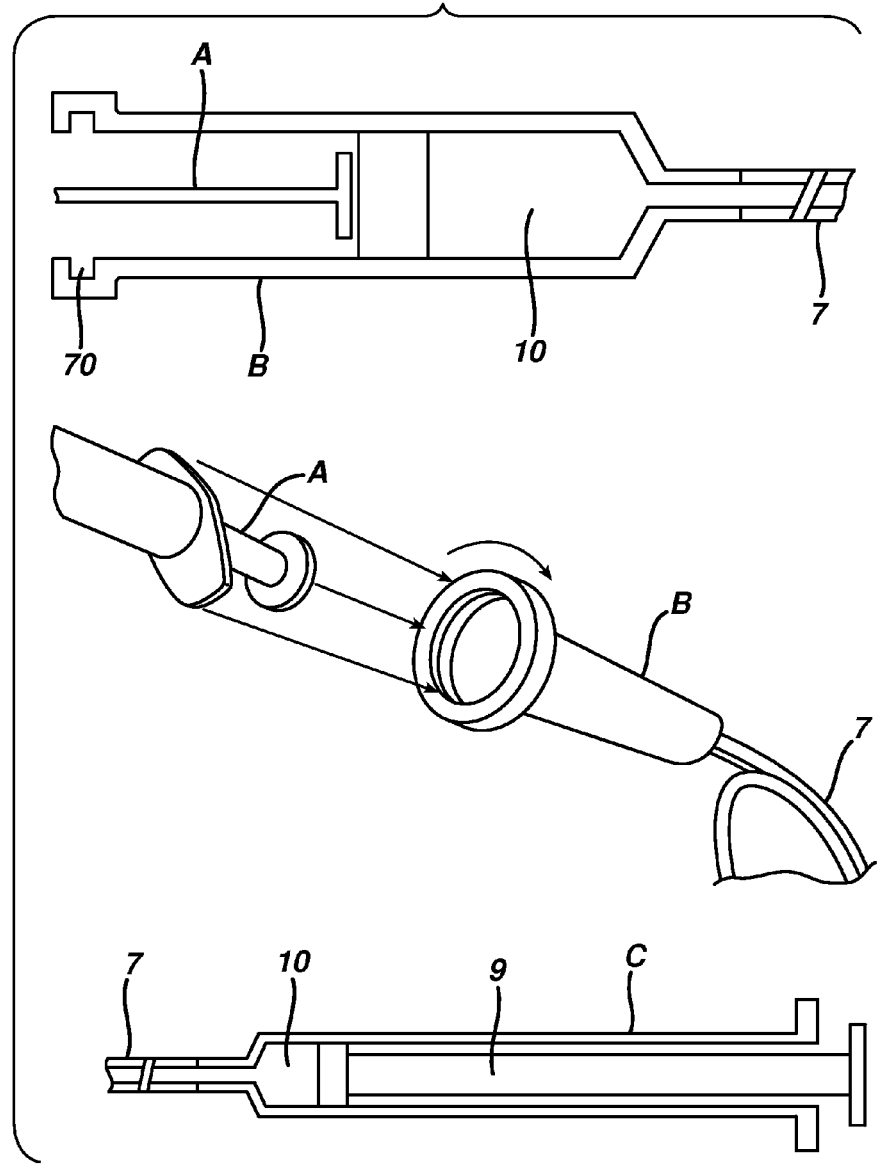

The FIG. 7, it represents the syringe of force, the conduit (7) that transmits the pressure to the larger diameter device (B) and the way to place the plunger (A) of the injecting syringe that contains the material and the injection needle.

Figure 8:
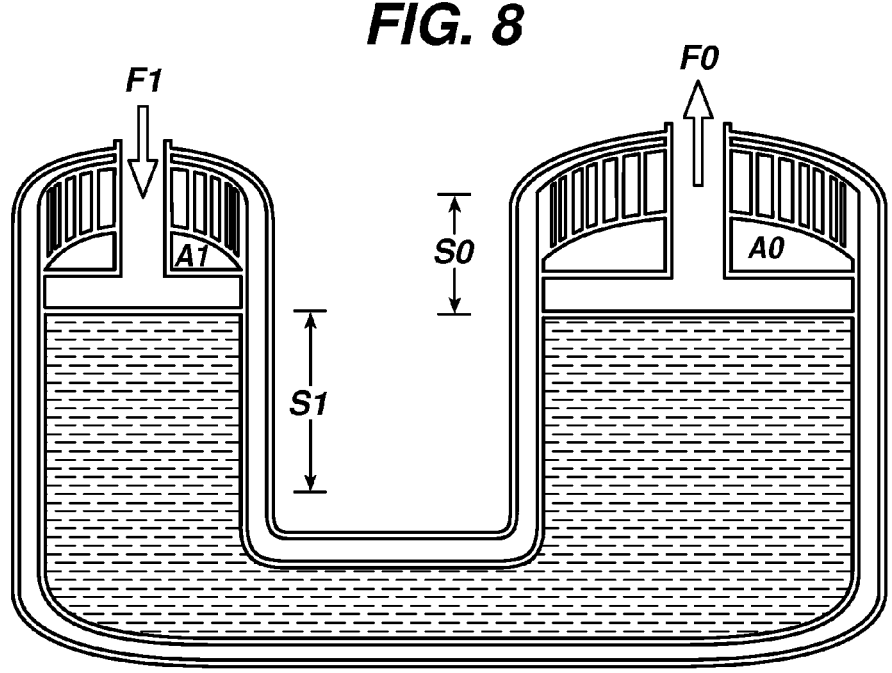

The FIG. 8, represents a hydraulic press, theoretical basic principles of the present invention.

Figure 9:
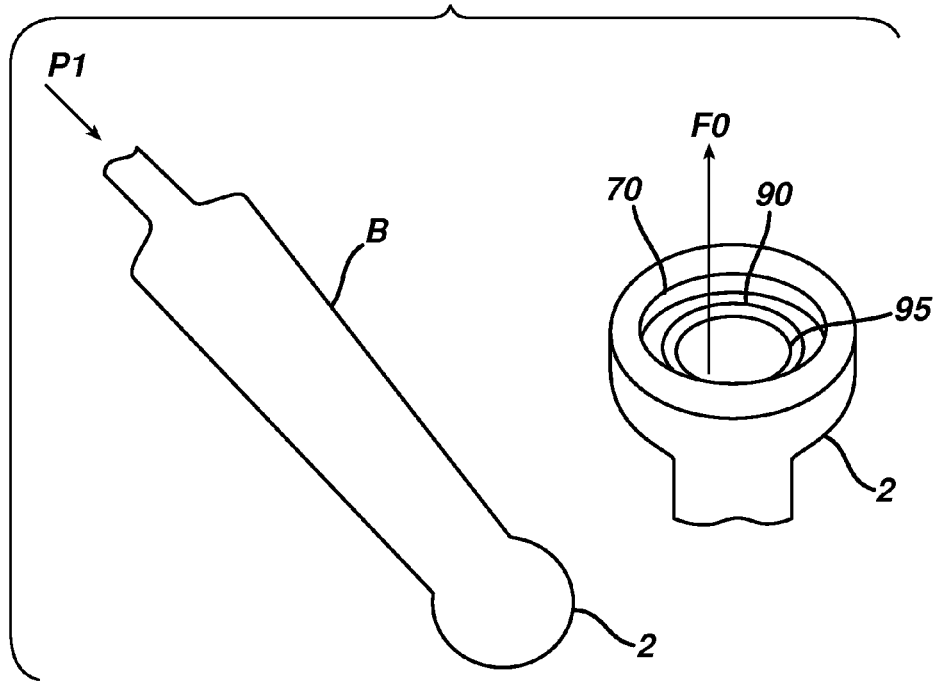

The FIG. 9, represents the pressure transmitted in the tube and the exit force generated, which pushes the plunger that injects the material through the needle.

DETAILED DESCRIPTION OF THE INVENTION

The present describes a new device and method to treat affections of the bones, specifically, in the treatment of osteoporotic or fractured vertebral bodies, These bone structures have different pathological states of diverse ethiology (trauma, osteoporosis, primary bone tumors or metastases, etc.). An alternative of treatment to stabilize and to consolidate this structures consists on the injection of a bio-materials such polymethylmethacrylate in the interior of the vertebral body for healing purpose.

The injection of biomaterials such as bone cement is carried out by means of a hydraulic device exerting pressure on small caliber conventional syringes connected directly to the needle; since the cement has the property of becoming hard quickly.

The theoretical basic principle for the operation of the device of the present invention consists on the amplification of the hydraulic pressure generated at distance and transmitted by the hydraulic tube.

In reference to the FIG. 8, the most frequent application to the Law of Pascal is the hydraulic press that consists of two asymmetric columns of liquid. This principle is applied in mechanical devices of engineering areas, this columns are different in the size or diameter of the transverse section. In accordance with the Law of Pascal, a pressure applied in one of the columns is transmitted entirely and in all directions. Therefore, if a force $F_1$ is applied on the area piston $A_1$, it will cause an exit force $F_0$ that acts on an area $A_0$ of the piston. This way, the entrance pressure is the same to the exit pressure, that is to say:

$$F_1/A_1 = F_0/A_0$$

The ideal mechanical advantage of the device is similar to the relationship of the exit force with regard to the entrance force.

$$VM = F_0/F_1 = A_0/A_1$$

Where a small entrance force can be multiplied ($A_0/A_1$ times) to produce a larger exit force ($F_0$), using an exit piston with a larger area than that of the entrance piston. The exit force will be given by:

$$F_0 = F_1 A_0/A_1$$

If friction is disregarded, in an ideal situation the entrance work should be the same to the exit work. Therefore, if the force $F_1$ travels a distance $S_1$ while the exit force $F_0$ travels a distance $S_0$, there is equality.

$$F_1 S_1 = F_0 S_0$$

The mechanical advantage can be expressed in terms of the distances traveled by the pistons:

$$VM = F_0/F_1 = S_1/S_0$$

It is observed that the mechanical advantage is obtained at expenses of the distance that the entrance piston travels.

In reference to the FIG. 9 that describes the body (B) and area (95) of the piston of larger area of the present invention, it is also represented the entrance of the pressure $P_1$ that is transmitted through the incompressible fluid, either water or oil, content in the flexible tube (not shown) that generates an exit force $F_0$. The attachment (2) for the lateral wings of the injecting syringe that contains the bone cement acts as coupler to the device, the wings enter tightly in the internal peripheral groove (70) diametrically opposed inside the bolster(header) of the body of the device object of the present invention, with a turn of 90° either clockwise or counterclockwise. The plunger of the syringe enters in the longitudinal central space (95) of the body (B).

Figure 1:
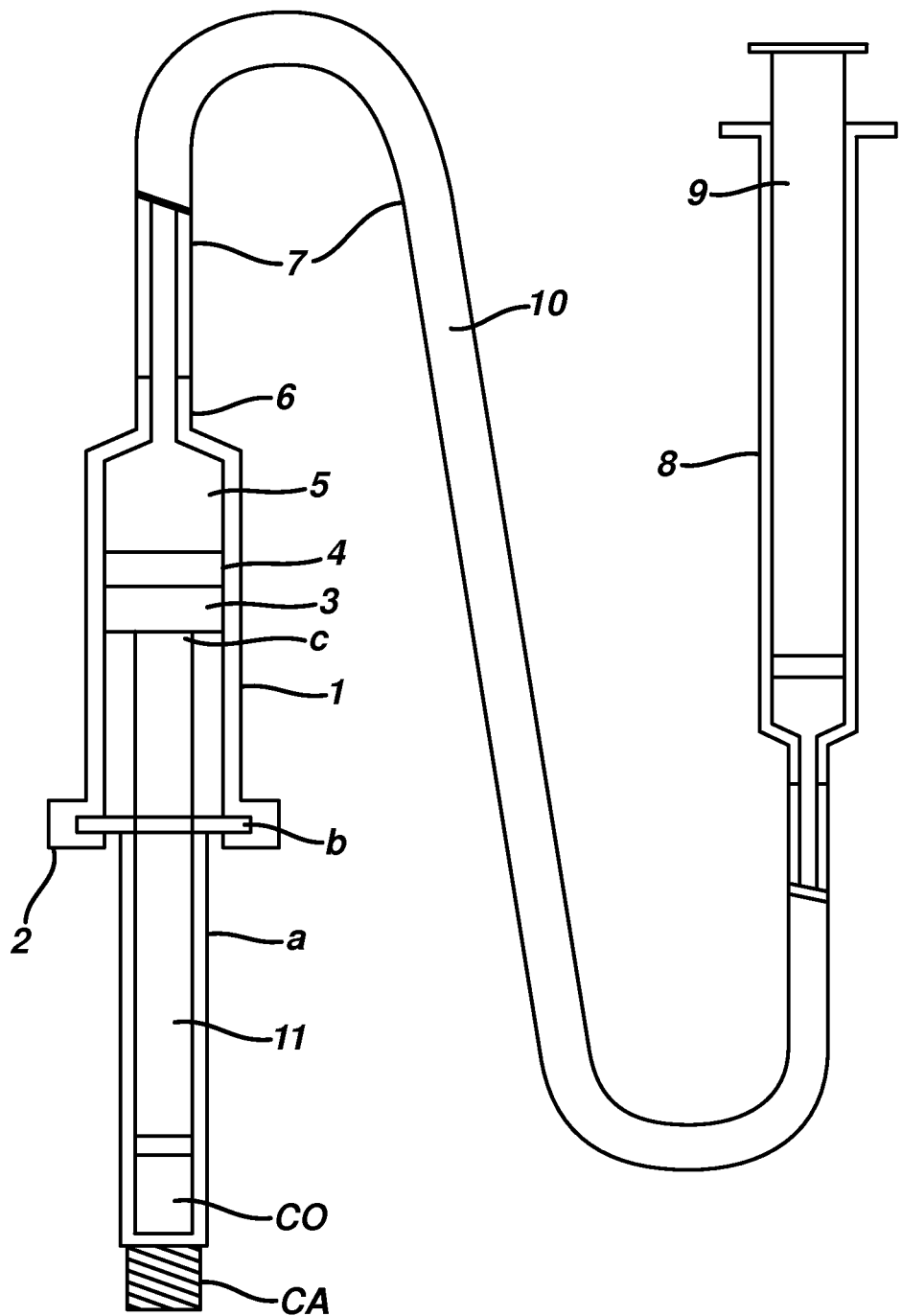

Returning to the FIG. 1, the hydraulic device consists of four main parts arranged one after another in such a way that allows to inject at distance and in a controlled way (regarding the pressure) viscous materials such as polymehylmethacrylate used in percutaneous vertebroplasty for the reestablishment (without surgery) of patient with osteoporotic fractures.

The device here described is designed to inject at distance a polymethylmethacrylate suspension with viscous consistency, directly in the cancellous bone of the vertebral bodies by means of a syringe loaded with the bone cement attached to a bone biopsy needle. The device consists of four main parts, "injecting syringe" in vicinity to the patient, "pressure" exerting body, "hydraulic transmission tube" and "manual syringe". in this, the fingers of the operator exercise the controlled force. This control is carried out by the operator's tact sensitivity. This device conforms a hydraulic system for polymethylmethacrylate injection at a variable distance from the patient (usually 1 m to 1.5 m).

The injection part is a commercially available, disposable 3 ml. hypodermic syringe (a) that is placed next to the patient, loaded with the bone cement that consists of a plunger (11) that pushes the material (CO) to be injected in the vertebral body trough a bone needle (CA), (not shown). This syringe couples tightly in a revolved way, by means of the opposed wings of support (b), in a peripheral groove in the internal face of the bolster (2) of the body of pressure, it is coupled by means of the opposed wings (b) used as support for the fingers in an act of usual injection, these wings (b) are placed in the entrance guide and rotated, either clockwise or counterclockwise an angle of 90° to stay in tightly fixed to avoid inadvertent detachment and loss of the pressure. The injection needle is coupled rotating the threaded distal end (CA) in the usual way of common plastic syringes in order to avoid spillage of the material to be injected due to the high pressure exercised on the plunger (c) and its end (3). For exchange, the empty syringe is detached from the needle, and then from the pressure device by means of a 90° rotation, discarded (2) and replaced with another loaded syringe prepared in advance and stored in a cold environment to delay curing and hardening of the cement. The syringe (a) is of 3 or 5 ml capacity.

The part of pressure, consists of distal inverted syringe body (1) of larger diameter that the syringe at the proximal end of the complete device, It has a bolster (2) open to the atmospheric pressure that contains an internal peripheral groove where the opposed supporting wings of the injecting disposable hypodermic syringe are coupled (b) with a turn of 90°. Its interior is open to the atmospheric pressure and receives the plunger of the injecting syringe (c) in a extended position to make contact with the rigid surface of the piston (3), The piston moves tightly with respect of the internal wall of the device (1) by means of a rubber cap (4), to maintain a closed hydraulic space (5) The distal pressure is transmitted to the piston through the opening or mouthpiece (6) connected to the flexible tube of polyethylene or similar material (7) by means of the hydraulic fluid (10). The rigid surface of the piston (3) exercises pressure (which has been increased by the device) on the plunger (11) of the injecting syringe. The body (1) is manufactured of transparent plastic, aluminum or any other suitable light-weighted and rigid material. Other characteristics of the body will be described (1) with more detail in the FIGS. 5, 7 and 9.

The hydraulic tube for pressure transmission (the Pascal's Principle), is a tube or flexible hose of polyethylene or similar material of little weight, with appropriate diameter to couple in the distant and proximal ends of the syringes, the longitude is variable, most commonly of 1.0 m to 1.50 m, it is resistant to the internal pressure. The tube is loaded of water, oil or other non-compress fluid (10) to integrate together with the manual proximal syringe and the body of pressure closed hydraulic system.

The manual syringe (8), has a smaller diameter than the body of pressure (1) in a 2/1, 3/1 or 4/1 ratio that may vary according to the necessity of each case. According to the hydraulic press described in the FIG. 8, the longitude of the manual syringe should be larger than that of the body of pressure (1) with the purpose of containing enough volume to displace the piston the, distance required to impel the plunger of the injecting syringe. this way, the quantity required of bone cement is deposited in the vertebral body.

The device works in the following way: a manual force is exercised on the plunger (9) of the manual syringe (8) in its extended position, the force exercises a pressure that is transmitted through the incompressible fluid (10) content in the flexible tube and in the camera (5) of the body of pressure (1). This pressure exercises an increased force on the plunger of the injecting syringe, due to the mechanical advantage of the relationship of areas or displacements formerly described. The plunger of the injecting syringe in turn, exert a force that impels (to) the material or cement to be injected in the patient's vertebral body through the bone biopsy needle. Once the total amount or content of the injecting syringe has been delivered, the plunger of the manual syringe is retracted to generate space inside the body of pressure (1) by retracting the piston to replace the emptied syringe with a loaded new syringe to continue the injection. Up to 10 ml. of bone cement is required to achieve an suitable filling of the fractured vertebral body, therefore, 3 to 4 syringe exchanges may be necessary.

The bone needle stays in place during the procedure that is to say, the movements or abnormal displacements of the needle during the injection are avoided, situation that implies several advantages: For the patient, since additional punctures are less frequent and for the operator with less problems of solidification of the cement.

Another advantage of the device is that the transmission of the pressure is immediate, that is to say, doesn't have a dynamic memory by effects of the increasing viscosity due to the solidification in the injection conduit specially with prolonged injections, prone to happen in the injecting devices of the previous technique that are loaded with the complete volume of cement to be placed. On the other hand, the threaded plunger doesn't allow tact sensibility regarding the exercised pressure and therefore favors unwanted leakage of the bone cement due to the dynamic memory of the material.

Figure 2:
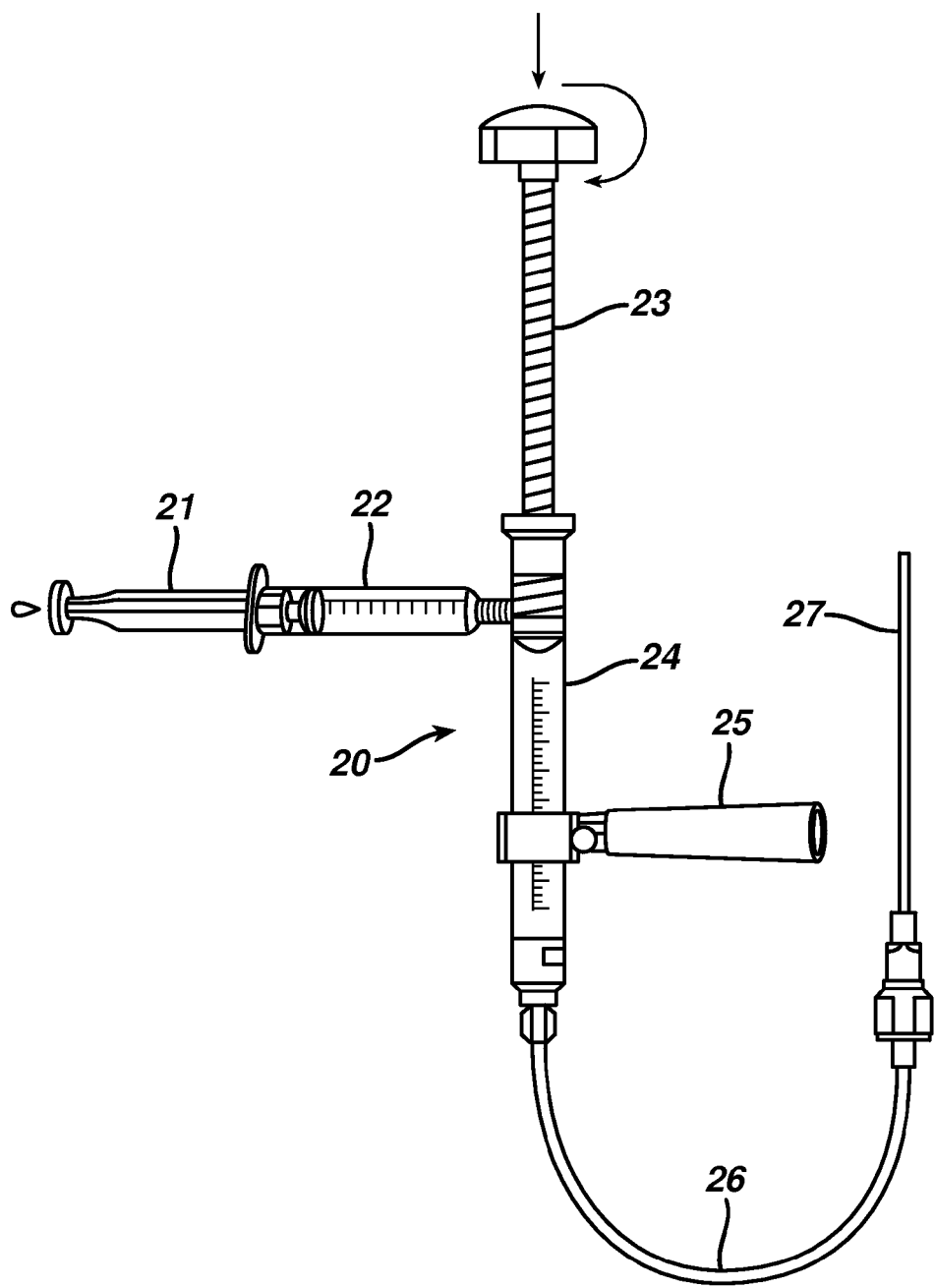

To this respect we have devices of the previous technique such as the (20) FIG. 2 that consists of a threaded plunger (23) that impels the contained cement in the camera (24) and a refilling deposit (22) that in turn feeds the camera by means of a plunger (21); A handle (25) that serves for support to the other hand of the operator to facilitate exercise the intense force so that the cement flows in a short tube (26) and it is injected through the needle (27).

The device (30) of the previous technique of the FIG. 3 contains two cameras (35) (32) connected by a valve check in the conduit (37). The bone cement is mixed In the camera (35) and impelled to the injection camera (32) by means of a plunger(36), once in the injection camera the cement is impelled by the piston (38) of a plunger (34) moved by a lever that provides the required force (33), forcing the cement through the opening (31) that in turn contains a valve check that closes in the recharge operation.

The FIG. 4 illustrate another device (40) of the previous technique for injection of polymethylmethacrylate. In this one the threaded plunger (41) has a crank (42) in the end to facilitate impel the total content of the syringe (45), and supporting elements (43) (44) for the other hand of the operator in the action of injection of the bone cement.

The FIG. 5, represents a cut profile and front view the body of pressure (50) that shows the groove of the bolster (2) where the injecting syringe that contains the bone cement is secured. Also presents the front view and profile of the piston (51) and the rubber cap (52) that avoids spillage of the hydraulic fluid in the action of transmission of the pressure. With this body of pressure, object of the present invention, is possible to transmit the pressure at distance and therefore reduces exposure of the operator to secondary ionizing radiation coming from the patient at the time of placement of the bone cement. This body of pressure complies with the characteristic of being light-weighted, may be disposable or reusable, manufactured of plastic, aluminum or other suitable material able to support sterilization.

The FIG. 6, represents frontal and lateral views of the manual or impulsion syringe (60), and plunger (61) where the rubber cap is placed (62) to avoid leakage of the hydraulic fluid. The bone cement should be kept in a cold environment before it is applied so it is maintain fluid to avoid solidification in the needle.

In the FIG. 7, the transverse cut of the cylindrical hollow body of pressure is described (B) that houses the plunger (A) of the injecting syringe secured in the peripheral groove (70) of this body of pressure, it is connected to the flexible tube (7) that transmits the hydraulic pressure (10), exercised from the manual or impulsion syringe (C) by means of its plunger (9). Here is illustrated the way the injecting syringe is attached to the body of pressure, Once introduced the plunger (A) in the opening of the body of pressure (B) the syringe is turned 90° in such a way that the body of the syringe is tightly secured to proceed with the injection of the bone cement.

The use of small diameter syringes in the application of the cement has the advantage of less resistance to flow, so a more viscous cement can be injected to reduce the possibilities of leakage from the vertebral body.

The experts in the technique expect other embodiments of the invention might exist, that is to say, embodiments of instruments built according to the teachings of the present invention. Because many of the characteristics of the embodiments are similar to those previously described. Peculiar embodiments of the invention have been illustrated and described in those that it will be obvious for those experts in the technique that several modifications or changes can be made without leaving the reach of the present invention. The above-mentioned tries to cover with the added claims so that the changes and modifications fall inside the reach of the present invention.

The invention claimed is:

1. A method of injecting a viscous material into a patient, the method comprising: providing a delivery device having: an injector body having a reservoir and an exit port in communication with the reservoir, the reservoir containing a viscous bone cement prior to the bone cement having set; a hydraulic tube connected to the body; a hydraulic actuator connected to the hydraulic tube and having a vessel, the vessel containing an incompressible fluid, the hydraulic actuator configured to pressurize the incompressible fluid to apply a force through the hydraulic tube to the injector body to force the viscous bone cement through the exit port; wherein the injector body, hydraulic tube, and hydraulic actuator are configured as a hydraulic press such that a force applied to the hydraulic actuator results in an increased force applied to the viscous bone cement; and applying a force to the hydraulic actuator to drive a flow of viscous bone cement from the reservoir and into the patient at a force that is increased with respect to the force applied to the hydraulic actuator, wherein applying the force to the hydraulic actuator comprises moving a first drive element extending into the vessel of the hydraulic actuator from a first, retracted position to a second, advanced position to drive the flow of viscous bone cement into the patient, wherein the delivery device further comprises a second drive element disposed in the injector body and having a first end that includes a first sealing member for preventing hydraulic fluid from flowing into the reservoir, wherein a portion of the injector body having the first end of the second drive element disposed therein has a diameter that is greater than a diameter of the reservoir, wherein when the force is applied to the hydraulic actuator, a distance traveled by the first drive element is greater than a distance traveled by the second drive element.

2. The method of claim 1, wherein the hydraulic actuator comprises a linear actuator.

3. The method of claim 1, wherein the hydraulic actuator comprises a syringe.

4. The method of claim 1, wherein a longitudinal distance traveled by the first drive element between the first, retracted position and the second, advanced position is greater than a length of the injector body, the length being measured in the direction of the force applied to the hydraulic actuator.

5. The method of claim 1, wherein the hydraulic tube has a length selected so that the hydraulic actuator is positioned about 1 to 1.5 meters away from the injector body.

6. The method of claim 1, wherein the hydraulic tube is substantially flexible.

7. The method of claim 1, further comprising cooling the viscous bone cement in a manner sufficient to delay its hardening.

8. The method of claim 1, further comprising cooling the viscous bone cement, prior to placing the bone cement in the injector body, in a manner sufficient to delay its hardening.

9. The method of claim 1, wherein, prior to a start of injection of the viscous bone cement into the patient, the reservoir holds about 3 to 5 ml of cement therein.

10. The method of claim 1, wherein the injection site is located within a vertebra.

11. The method of claim 1, further comprising applying a fluoroscopic field to at least a portion of the patient and positioning the hydraulic actuator outside of the fluoroscopic field.

12. The method of claim 1, wherein a second end of the second drive element comprises a second sealing member that directly contacts the viscous bone cement in the reservoir, a diameter of the first sealing member being greater than a diameter of the second sealing member.

13. The method of claim 1, wherein the second end of the second drive element comprises a piston that directly contacts the viscous bone cement in the reservoir.

14. The method of claim 1, further comprising positioning a first end of an injection needle within a vertebra and coupling a second end of the injection needle to the exit port of the injector body so that when the force is applied to the hydraulic actuator, the viscous bone cement flows out of the exit port, through the injection needle, and into the patient's vertebra.

15. The method of claim 14, further comprising, after applying the force to the hydraulic actuator to inject the viscous bone cement into the patient, detaching the injection needle from the injector body and loading the reservoir with a second quantity of bone cement without removing the injection needle from the patient.

16. The method of claim 1, wherein the viscous bone cement comprises polymethyl methacrylate (PMMA) bone cement.

* * * * *